US008414932B2

(12) United States Patent
Nalepa et al.

(10) Patent No.: US 8,414,932 B2
(45) Date of Patent: *Apr. 9, 2013

(54) ACTIVE BROMINE CONTAINING BIOCIDAL COMPOSITIONS AND THEIR PREPARATION

(75) Inventors: Christopher J. Nalepa, Zachary, LA (US); Robert M. Moore, Jr., Baton Rouge, LA (US)

(73) Assignee: Albemarle Corporation, Baton Rouge, LA (US)

(*) Notice: Subject to any disclaimer, the term of this patent is extended or adjusted under 35 U.S.C. 154(b) by 1045 days.

This patent is subject to a terminal disclaimer.

(21) Appl. No.: 10/282,290

(22) Filed: Oct. 28, 2002

(65) Prior Publication Data

US 2004/0022874 A1 Feb. 5, 2004

Related U.S. Application Data

(63) Continuation-in-part of application No. 09/506,911, filed on Feb. 18, 2000, now Pat. No. 6,511,682, and a continuation-in-part of application No. 09/456,781, filed on Dec. 8, 1999, now Pat. No. 6,495,169, and a continuation-in-part of application No. 09/451,319, filed on Nov. 30, 1999, and a continuation-in-part of application No. 09/974,622, filed on Oct. 9, 2001, now Pat. No. 6,652,889, said application No. 09/506,911 is a continuation-in-part of application No. 09/404,184, filed on Sep. 24, 1999, now Pat. No. 6,322,822, and a continuation-in-part of application No. 09/088,300, filed on Jun. 1, 1998, now Pat. No. 6,068,861, said application No. 09/404,184 is a continuation-in-part of application No. 09/088,300, said application No. 09/456,781 is a continuation of application No. 09/088,300, said application No. 09/451,319 is a continuation-in-part of application No. 09/088,300, said application No. 09/974,622 is a continuation-in-part of application No. 09/404,184, and a continuation-in-part of application No. 09/506,911, and a continuation-in-part of application No. 09/088,300.

(51) Int. Cl.
*A01N 39/00* (2006.01)
*A01N 59/02* (2006.01)
*A01N 59/08* (2006.01)
*A01N 59/00* (2006.01)

(52) U.S. Cl. ........ 424/703; 424/615; 424/663; 424/665; 424/680; 424/423

(58) Field of Classification Search .................. 424/661, 424/703, 663, 615, 665, 680, 723
See application file for complete search history.

(56) References Cited

U.S. PATENT DOCUMENTS 1,995,639 A 3/1935 Henderson
2,184,886 A 12/1939 Muskat et al.
2,184,888 A 12/1939 Muskat et al.
2,443,429 A 6/1948 Marks et al.
2,580,808 A 1/1952 Marks et al.
2,662,855 A 12/1953 Kamlett
2,779,764 A 1/1957 Paterson
2,815,311 A 12/1957 Ellis et al.
2,913,460 A 11/1959 Brown et al.
2,929,816 A 2/1960 Chamberlain
2,971,959 A 2/1961 Waugh et al.
3,147,254 A 9/1964 Paterson
3,147,259 A 9/1964 Paterson
3,152,073 A 10/1964 Morton ........................ 210/62
3,170,883 A 2/1965 Owen et al. .................. 252/187
3,222,276 A 12/1965 Belohlav et al.
3,308,062 A 3/1967 Gunther ........................ 210/58
3,328,294 A 6/1967 Self et al. ........................ 210/62
3,412,021 A 11/1968 Paterson
3,429,668 A 2/1969 Gaska et al.
3,519,569 A 7/1970 Diaz
3,558,503 A 1/1971 Goodenough et al. ........ 252/187
3,589,859 A 6/1971 Foroulis ......................... 21/2.7
3,711,246 A 1/1973 Foroulis ......................... 21/2.7
3,749,672 A 7/1973 Golton et al. .................. 252/95
3,767,586 A 10/1973 Rutkiewic
3,850,833 A 11/1974 Koceich et al.
4,032,460 A 6/1977 Zilch et al. ................. 252/8.55 B
4,235,599 A 11/1980 Davis et al.
4,237,090 A 12/1980 DeMonbrun et al. ........... 422/13
4,295,932 A 10/1981 Pocius ......................... 162/161
4,297,224 A 10/1981 Macchiarolo et al.
4,382,799 A 5/1983 Davis et al. ..................... 8/107

(Continued)

FOREIGN PATENT DOCUMENTS

AU 1802392 B 12/1995
CA 2071076 A1 12/1992

(Continued)

OTHER PUBLICATIONS

Clare, A..S., "Marine Natural Product Antifoulants: Status and Potential," Biofouling (1996) 9: 211-229.

(Continued)

*Primary Examiner* — Alton Pryor
(74) *Attorney, Agent, or Firm* — Marcy M. Hoefling

(57) ABSTRACT

Described are highly concentrated liquid biocidal solutions formed in water from (a) specified bromine sources (e.g., BrCl or mixtures of BrCl and $Br_2$) and (b) alkali metal salt of sulfamic acid and/or sulfamic acid and alkali metal base, wherein the solution contains >160,000 ppm of active bromine. Solutions of this type have been found to have greater stability than a commercially-available solution made from the same components containing 148,600 ppm of active bromine. Also described are new, water-soluble, solid state biocidal products formed by removing the water from solutions made in water from (a) and (b) irrespective of the initial concentration of active bromine. Removal of water can be accomplished by flashing or distillation at reduced pressure or preferably by spray drying. Such solid state products are typically in the form of powders or small particles, but can be compacted into larger forms preferably with the aid of one or more suitable binding agents.

17 Claims, No Drawings

U.S. PATENT DOCUMENTS

| | | | | |
|---|---|---|---|---|
| 4,392,799 | A | 7/1983 | Shikano et al. | |
| 4,427,435 | A | 1/1984 | Lorenz et al. | 71/67 |
| 4,451,376 | A | 5/1984 | Sharp | 210/701 |
| 4,465,598 | A | 8/1984 | Darlington et al. | 210/721 |
| 4,476,930 | A | 10/1984 | Watanabe | 166/279 |
| 4,490,308 | A | 12/1984 | Fong et al. | 260/513 N |
| 4,491,507 | A | 1/1985 | Herklotz et al. | |
| 4,539,071 | A | 9/1985 | Clifford et al. | 162/161 |
| 4,546,156 | A | 10/1985 | Fong et al. | 526/240 |
| 4,557,926 | A | 12/1985 | Nelson et al. | |
| 4,566,973 | A | 1/1986 | Masler, III et al. | 210/701 |
| 4,595,517 | A | 6/1986 | Abadi | 252/82 |
| 4,595,691 | A | 6/1986 | LaMarre et al. | 514/367 |
| 4,604,431 | A | 8/1986 | Fong et al. | 525/351 |
| 4,642,194 | A | 2/1987 | Johnson | 210/699 |
| 4,643,835 | A | 2/1987 | Koeplin-Gall et al. | 210/754 |
| 4,661,503 | A | 4/1987 | Martin et al. | 514/372 |
| 4,680,339 | A | 7/1987 | Fong | 525/54.11 |
| 4,680,399 | A | 7/1987 | Buchardt | 546/139 |
| 4,703,092 | A | 10/1987 | Fong | 525/351 |
| 4,711,724 | A | 12/1987 | Johnson | 210/699 |
| 4,752,443 | A | 6/1988 | Hoots et al. | 422/13 |
| 4,759,852 | A | 7/1988 | Trulear | 210/699 |
| 4,762,894 | A | 8/1988 | Fong et al. | 525/344 |
| 4,777,219 | A | 10/1988 | Fong | 525/329.4 |
| 4,801,388 | A | 1/1989 | Fong et al. | 210/701 |
| 4,802,990 | A | 2/1989 | Inskeep, Jr. | 210/699 |
| 4,822,513 | A | 4/1989 | Corby | 252/106 |
| 4,846,979 | A | 7/1989 | Hamilton | 210/754 |
| 4,872,999 | A | 10/1989 | Schild et al. | |
| 4,883,600 | A | 11/1989 | MacDonald et al. | 210/696 |
| 4,886,915 | A | 12/1989 | Favstritsky | 564/503 |
| 4,898,686 | A | 2/1990 | Johnson et al. | 252/389.2 |
| 4,906,651 | A | 3/1990 | Hsu | 514/372 |
| 4,923,634 | A | 5/1990 | Hoots et al. | 252/389.2 |
| 4,929,424 | A | 5/1990 | Meier et al. | 422/9 |
| 4,929,425 | A | 5/1990 | Hoots et al. | 422/13 |
| 4,966,716 | A | 10/1990 | Favstritsky et al. | 210/755 |
| 4,992,209 | A | 2/1991 | Smyk et al. | 252/387 |
| 4,995,987 | A | 2/1991 | Whitekettle et al. | 210/754 |
| 5,034,155 | A | 7/1991 | Soeder et al. | 252/389.23 |
| 5,035,806 | A | 7/1991 | Fong et al. | 210/701 |
| 5,047,164 | A | 9/1991 | Corby | 252/106 |
| 5,055,285 | A | 10/1991 | Duncan et al. | 423/473 |
| 5,118,426 | A | 6/1992 | Duncan et al. | 210/721 |
| 5,120,452 | A | 6/1992 | Ness et al. | 210/754 |
| 5,120,797 | A | 6/1992 | Fong et al. | 525/329.4 |
| 5,130,033 | A | 7/1992 | Thornhill | |
| 5,141,652 | A | 8/1992 | Moore, Jr. et al. | 210/754 |
| 5,179,173 | A | 1/1993 | Fong et al. | 525/329.4 |
| 5,192,459 | A | 3/1993 | Tell et al. | 252/106 |
| 5,194,238 | A | 3/1993 | Duncan et al. | 423/473 |
| 5,196,126 | A | 3/1993 | O'Dowd | 210/754 |
| 5,202,047 | A | 4/1993 | Corby | 252/106 |
| 5,209,934 | A | 5/1993 | Ekis, Jr. et al. | |
| 5,259,985 | A | 11/1993 | Nakanishi et al. | 252/180 |
| 5,264,136 | A | 11/1993 | Howarth et al. | 210/754 |
| 5,389,384 | A | 2/1995 | Jooste | 424/661 |
| 5,414,652 | A | 5/1995 | Mieda et al. | 365/122 |
| 5,424,032 | A | 6/1995 | Christensen et al. | 422/14 |
| 5,429,723 | A | 7/1995 | Atkinson | |
| 5,443,849 | A | 8/1995 | Corby | 424/667 |
| 5,460,833 | A | 10/1995 | Andrews et al. | |
| 5,464,636 | A | 11/1995 | Hight et al. | 424/661 |
| 5,525,241 | A | 6/1996 | Clavin et al. | 210/753 |
| 5,527,547 | A | 6/1996 | Hight et al. | 424/661 |
| 5,565,109 | A | 10/1996 | Sweeny | |
| 5,589,106 | A | 12/1996 | Shim et al. | 252/387 |
| 5,607,619 | A | 3/1997 | Dadgar et al. | 252/187.2 |
| 5,679,239 | A | 10/1997 | Blum et al. | 205/556 |
| 5,683,654 | A | 11/1997 | Dallmier et al. | 422/14 |
| 5,688,515 | A | 11/1997 | Kuechler et al. | |
| 5,795,487 | A | 8/1998 | Dallmier et al. | 210/754 |
| 5,900,512 | A | 5/1999 | Elnagar et al. | 568/14 |
| 5,922,745 | A | 7/1999 | McCarthy et al. | 514/372 |
| 5,942,126 | A | 8/1999 | Dallmier et al. | 210/756 |
| 6,007,726 | A | 12/1999 | Yang et al. | 210/752 |
| 6,015,782 | A | 1/2000 | Petri et al. | 510/379 |
| 6,037,318 | A | 3/2000 | Na et al. | 510/379 |
| 6,068,861 | A | 5/2000 | Moore, Jr. et al. | 424/703 |
| 6,069,142 | A | 5/2000 | Gaffney et al. | |
| 6,086,861 | A | 7/2000 | Onitsuka et al. | |
| 6,110,387 | A | 8/2000 | Choudhury et al. | 210/752 |
| 6,123,870 | A * | 9/2000 | Yang et al. | 252/186.1 |
| 6,136,205 | A | 10/2000 | Dallmier et al. | |
| 6,156,229 | A * | 12/2000 | Yang et al. | 252/186.1 |
| 6,270,722 | B1 | 8/2001 | Yang et al. | 422/37 |
| 6,287,473 | B1 | 9/2001 | Yang et al. | 210/754 |
| 6,299,909 | B1 * | 10/2001 | Moore et al. | 424/703 |
| 6,306,441 | B1 * | 10/2001 | Moore et al. | 424/703 |
| 6,322,749 | B1 | 11/2001 | McCarthy et al. | |
| 6,322,822 | B1 * | 11/2001 | Moore et al. | 424/703 |
| 6,348,219 | B1 * | 2/2002 | Torres et al. | 424/703 |
| 6,352,725 | B1 * | 3/2002 | Torres et al. | 424/703 |
| 6,375,991 | B1 * | 4/2002 | Moore, Jr. | 424/703 |
| 6,419,879 | B1 | 7/2002 | Cooper et al. | |
| 6,423,267 | B1 | 7/2002 | Yang et al. | 422/37 |
| 6,471,974 | B1 | 10/2002 | Rees et al. | |
| 6,478,972 | B1 | 11/2002 | Shim et al. | |
| 6,506,418 | B1 * | 1/2003 | McKinnie et al. | 424/703 |
| 6,511,682 | B1 * | 1/2003 | Moore et al. | 424/703 |
| 6,533,958 | B2 | 3/2003 | Shim et al. | |
| 6,652,889 | B2 * | 11/2003 | Moore et al. | 424/703 |
| 6,660,307 | B2 | 12/2003 | Zolotarsky et al. | |
| 6,669,904 | B1 | 12/2003 | Yang et al. | |
| 6,740,253 | B2 | 5/2004 | Vohra et al. | |
| 7,087,251 | B2 * | 8/2006 | Nalepa | 424/703 |
| 7,195,782 | B2 | 3/2007 | Moore et al. | |
| 7,204,931 | B2 | 4/2007 | Martin et al. | |
| 2001/0004461 | A1 | 6/2001 | Moore, Jr. et al. | |
| 2004/0022874 | A1 | 2/2004 | Nalepa et al. | |
| 2004/0120853 | A1 | 6/2004 | Carpenter et al. | |
| 2005/0061197 | A1 | 3/2005 | Nalepa | |
| 2005/0147696 | A1 | 7/2005 | Moore, Jr. et al. | |
| 2006/0278586 | A1 | 12/2006 | Nalepa et al. | |
| 2008/0146641 | A1 | 6/2008 | Urano et al. | |

FOREIGN PATENT DOCUMENTS

| | | |
|---|---|---|
| EP | 0524721 A1 | 1/1993 |
| EP | 1 080 641 A2 | 3/2001 |
| GB | 644 | 0/1910 |
| GB | 365558 | 1/1932 |
| GB | 526952 | 10/1940 |
| GB | 763383 | 12/1956 |
| GB | 1 355 359 | 6/1974 |
| GB | 2 302 687 | 1/1997 |
| JP | 2001226209 A | 8/2001 |
| RU | 2082659 C1 | 6/1997 |
| WO | WO 89/10696 | 11/1989 |
| WO | 9015780 | 12/1990 |
| WO | WO 96/14092 A1 | 5/1996 |
| WO | WO 96/30562 | 10/1996 |
| WO | 9720546 | 6/1997 |
| WO | 9720909 | 6/1997 |
| WO | 9734827 | 9/1997 |
| WO | 9743392 | 11/1997 |
| WO | 9815609 | 4/1998 |
| WO | 9906320 | 2/1999 |
| WO | 9932596 | 7/1999 |
| WO | 9955627 | 11/1999 |
| WO | WO 99/62339 | 12/1999 |
| WO | 0034186 | 6/2000 |
| WO | WO 00/58532 | 10/2000 |
| WO | 0120996 A1 | 3/2001 |
| WO | WO 03/093171 | 11/2003 |

OTHER PUBLICATIONS

S. Tsukamoto, et al., "Ceratinamides A and B: New Antifouling Dibromotyrosine Derivatives from the Marine Sponge *Pseudoceratina purpurea*," Tetrahedron (1996) 52: 8181-8186.

W. Miki, K. Kon-ya, and S. Mizobuchi, "Biofouling and Marine Biotechnology: New Antifoulants from Marine Invertebrates," Journal of Marine Biotechnology (1996) 4: 117-120.

H. Genthe, "The Incredible Sponge," Smithsonian (Aug. 1998) 29: 50-58.

M. Givskov, et al., "Eukaryotic Interference with Homoserine Lactone-Mediated Prokaryotic Signaling," Journal of Bacteriology (1996) 178: 6618-6622.

D. Ren, J.J. Sims, and T.K. Wood, "Inhibition of Biofilm Formation and Swarming of *Bacillus subtilus* by (5Z)-4-Bromo-5-(Bromomethylene)-3-Butyl-2(5H)-Furanone," Letters in Applied Microbiology (2002) 34: 293-299.

M.E. Weeks, "Discovery of the Elements: XVII. The Halogen Family," Journal of Chemical Education (1932) 9: 1915-1938.

A.J. Balard, Annales de Chemie et de Physique (1826), vol. 32, pp. 371-372.

H.S. Rzepa, "Elemental and Molecular Heritage: An Internet-Based Display," Molecules (1998) 3: 94-99.

B. Grinbaum and M. Friedman, "Bromine," in Kirk-Othmer Encyclopedia of Chemical Technology $4^{th}$ Ed. (New York, NY: John Wiley and Sons, Inc., 2001), vol. 4, pp. 548-549.

F. Yaron, "Bromine Manufacture: Technology and Economic Aspects," in "Bromine and Its Compounds," Z.E. Jolles, ed., pp. 3-12 (New York, NY: Academic Press, 1966).

"Bromine Brine," Arkansas Geological Commission, web address www.state.ar.us/agc/bromine.htm; 1 page.

R.D. Bartholomew, "Bromine-based Biocides for Cooling Water Systems: A Literature Review," Paper IWC 98-74 (Pittsburgh, PA: Engineers' Society of Western Pennsylvania, 1998), 30 pages.

F.W. Tanner and G. Pitner, "Germicidal Action of Bromine," Proceedings of the Society for Experimental Biology and Medicine (1939) 40: 143-145.

T.D. Beckwith and J.R. Moser, Journal of the American Water Works Association (1933) 25: 367-374.

D.R. Wood and E.T. Illing, Analyst (1930), Royal Society of Chemistry, The Analyst, 55: 126-127.

J. A. McCarthy, Journal of the New England Water Works Association (1944) 58: 55-68.

O. Wyss and R.J. Stockton, "The Germicidal Action of Bromine," Arch. Biochem. (1947) 12:267-271.

E.A. Shilov and J.N. Gladtchikova, "On the Calculation of the Dissociation Constants of Hypohalogenous Acids from Kinetic Data," Journal of the American Chemical Society (1938) 60: 490-491.

G.M. Fair, et al., "The Behavior of Chlorine as a Water Disinfectant," Journal of the American Water Works Association (1948) 40: 1051-1061.

E.K. Rideal and U.R. Evans, "The Effect of Alkalinity on the Use of Hypochlorites," Journal of the Society of the Chemical Industry (1921) 40: 64R-66R.

C.K. Johns, "Germicidal Power of Sodium Hypochlorite," Industrial and Engineering Chemistry (1934) 26: 787-788.

G.R. Dychala, "Chlorine and Chlorine Compounds" in Disinfection, Sterilization, and Preservation $4^{th}$ Ed., S.S. Block, ed., pp. 137-138 and 149-15, (Philadelphia, PA, Lea & Febiger, 1991).

T. Kristoffersen and I.A. Gould, "Effect of Sodium Bromide on the Bactericidal Effectiveness of Hypochlorite Sanitizers of High Alkalinity," Journal of Dairy Science (1958) 41: 950-955.

G.U Houghton, "Bromine Content of Underground Waters. II. Observations on the Chlorination of Water Containing Free Ammonia and Naturally Occurring Bromide", Journal of the Society of the Chemical Industry (1946) 65: 324-328.

H. Farkas-Himsley, "Killing of Chlorine-Resistant Bacteria by Chlorine-Bromine Solutions," Applied Microbiology (1964) 12: 1-6.

P.W. Kabler, "Relative Resistance of Coliform Organisms and Enteric Pathogens in the Disinfection of Water with Chlorine," J. American Water Works Association (1951) 43: 553-560.

J.K. Johannesson, "The Bromination of Swimming Pools," American Journal of Public Health (1960) 50: 1731-1736.

J.D. Johnson and W. Sun, "Bromine Disinfection of Wastewater," in "Disinfection—Water and Wastewater," J.D. Johnson, ed., pp. 179-191 (Ann Arbor, MI: Ann Arbor Science, 1975).

J.K. Johannesson, "Anomalous Bactericidal Action of Bromamine," Nature (1958) 181: 1799-1780.

J.C. Albright, "Liquid Bromine Removes Obstinate Algae from 10,000 Gallon Tower for $2.10 a Day," Petroleum Processing (1948) 3: 421-422.

Y. Kott et al., "Effect of Halogens on Algae—III. Field Experiment," Water Research (1969) 3: 265-271.

N. Betzer and Y. Kott, "Effect of Halogens on Algae—II. *Cladophora* sp.," Water Research (1969) 3: 257-264. 14 pages.

Y. Kott and J. Edlis, "Effect of Halogens on Algae—I. *Chlorella sorokiniana*," Water Research (1969) 3: 251-256.

"Evolution of Industrial Water Treatment," Betz Handbook of Industrial Water Conditioning, Seventh Edition, pp. 7-15 (Trevose, PA: Betz Laboratories, Inc., 1976).

P.J. Sullivan and B.J. Hepburn, "The Evolution of Phosphonate Technology for Corrosion Inhibition," paper 496 (Houston, TX: NACE International, 1995), pp. 496/1-496/13.

W.A. Brungs, "Effects of Residual Chlorine on Aquatic Life," Journal of the Water Pollution Control Federation (1973) 45: 2180-2193.

A.T. Palin, "The Determination of Free and Combined Chlorine in Water by the Use of Diethyl-p-phenylene diamine," Journal of the American Water Works Association (1957) 49: 873-880.

C.W. Kruse, et al., "Halogen Action on Bacteria, Viruses, and Protozoa," in Proc. Natl. Specialty Conference on Disinfection, pp. 113-136 (New York, NY: ASCE, 1970).

R. Aull and T. Krell, "Design Features and their Affect on High Performance Fill," paper TP00-01 (Houston, TX: Cooling Technology Institute, 2000), pp. 1-31.

A.E. Gillam and R.A. Morton, "The Absorption Spectra of Halogens and Inter-Halogen Compounds in Solution in Carbon Tetrachloride," Proceedings of the Royal Society (London) (1929) vol. 124: 604-616.

S. Barratt and C.P. Stein, "On Bromine Chloride," Proceedings of the Royal Society (London) (1929) vol. 122: 582-588.

J.F. Mills, "Interhalogens and Halogen Mixtures as Disinfectants," in Disinfection—Water and Wastewater, J.D. Johnson, ed., pp. 113-143 (Ann Arbor, MI: Ann Arbor Science, 1975).

E.C. Wackenhuth and G. Levine, "An Investigation of Bromine Chloride as a Biocide in Condenser Water," (Pittsburgh, PA: Engineer's Society of Western Pennsylvania, 1974), pp. 1-14.

L.H. Bongers, T.P. O'Connor and D.T. Burton, "Bromine Chloride—An Alternative to Chlorine for Fouling Control in Condenser Cooling Systems," report No. EPA-600/7-77-053 (Research Triangle Park, NC: EPA Office of Research and Development, May 1977)., 5 pages.

B.H. Keswick, "Bromine-Chloride as an Alternative Disinfectant to Chlorine of Human Enteric Viruses and Other Pathogens in Water and Wastewater", Doctoral Dissertation, University of Hawaii (Ann Arbor, MI: University of Microfilms, 1979), 16 pages.

R.M. Moore, et al., "Use of a New Bromine-based Biocide in a Medium-Size Cooling Tower," paper IWC-97-51 (Pittsburgh, PA: Engineers' Society of Western Pennsylvania, 1997), 6 pages.

G.D. Nelson, "Chloramines and Bromamines," in Kirk Othmer Encyclopedia of Chemical Technology, vol. 5, pp. 565-580 (New York, NY: John Wiley and Sons, 1979).

Z. Zhang and J.V. Matson, "Organic Halogen Stabilizers: Mechanisms and Disinfection Efficiencies," paper TP89-05 (Houston, TX: Cooling Tower Institute. 1989), pp. 1-19.

J.C. Peterson, "Practical Air Washer Treatment in Synthetic Fiber Manufacturing Plants," paper IWC-87-39 (Pittsburgh, PA: Engineers' Society of Western Pennsylvania, 1987), pp. 366-370.

D. Vanderpool, M. Killoran, and R. Sergent, "Improving the Corrosion Inhibitor Efficiency of Tolyltriazole in the Presence of Chlorine and Bromine," paper 157 (Corrosion 87, San Francisco, CA , 1987), pp. 157/1-157/9.

C. Spurrell and J.S. Clavin, "Solid Halogen Donor Economically Answers the Challenge of SARA Title III and Corrosion Concerns," paper 474 (Corrosion 93, NACE Annual Conference and Corrosion Show, 1993), pp. 474/1-474/15.

A. Smith, et al., "Bromine vs. Gaseous Chlorine: A Comprehensive Review of Case Histories," paper 637 (Corrosion 93, NACE Annual Conference and Corrosion Show, 1993), pp. 637/1-637/12.

D.S. Larson, et al., "Improved Microbiological Control Using Halogen Donors in a Pasteurizer," MBAA Technical Quarterly (1993) 30: 173-178.

P. Sweeney, M. Ludensky, and O. Barokhov, "Mill Performance of a Brominated Methylethylhydantoin Slimicide," pp. 437-447, Proceedings of the 1999 TAPPI Papermakers Conference (Norcross, GA:: TAPPI, 1999).

F.J. Himpler, P.G. Sweeney, and M.L. Ludensky, "The Benefits of a Hydantoin-Based Slimicide in Papermaking Applications," APPITA Journal (Sep. 2001) 54: 427-430.

C.J. Nalepa, "New Bromine-Releasing Granules for Microbiological Control of Cooling Water," paper 03716 (Corrosion 2003 Houston, TX: NACE International, 2003), pp. 03716/1-03716/15.

M. Lewin and M. Avarahami, "The Decomposition of Hypochlorite-Hypobromite Mixtures in the pH Range 7-10," Journal of the American Chemical Society, (1955) 77: 4491-4498.

Z. Zhang, "Disinfection Efficiency and Mechanisms of 1-Bromo-3-Chloro-5,5-Dimethylhydantoin," Doctoral Dissertation, University of Houston, May 1988, pp. 160, 162, 163.

J.C. Conley, E..H. Puzig, and J.E. Alleman, "Bromine Chemistry—An Alternative to Dechlorination in Cooling Water and Wastewater Disinfection," IWC-87-42 (Pittsburgh, PA: Engineers' Society of Western Pennsylvania, 1987), pp. 389-395.

R.M. Moore, W.C. Lotz, and V.R. Perry, "Activated Sodium Bromide—Artificial Marsh Treatment: A Successful Plant-Wide Program," paper IWC-95-61 (Pittsburgh, PA: Engineers' Society of Western Pennsylvania, 1995). 12 pgs.

C.J. Nalepa, et al., "Case Study: Minimization of Corrosion Using Activated Sodium Bromide in a Medium-Size Cooling Tower," paper 485 (Corrosion 96 NACE International Annual Conference and Exposition, Houston, TX: Nace International, 1996), 485/1-485/485/12.

F.P. Yu, et al., "Cooling Tower Fill Fouling Control in a Geothermal Power Plant," paper 529 (Corrosion 98, Houston, TX: NACE International, 1998), p. 529/1-529-11.

F.P. Yu, et al., "Innovations in Fill Fouling Control," IWC-00-03 (Pittsburgh, PA: Engineers' Society of Western Pennsylvania, 2000), pp. 26-31.

T.C. Kuechler, et al., "Development of Monsanto's Towerbrom® Microbiocide, a New Bromine Microbiocide for Recirculating Water Systems," (McLean, VA: Association of Water Technologies, 1991), 1991 AWT Conference, p. 1-23.

T.C. Kuechler, A Towerbrom® Progress Report, (McLean, VA: Association of Water Technologies, 1993), pp. 1-15.

W.F. McCoy, et al., "Strategies Used in Nature for Microbial Fouling Control: Application for Industrial Water Treatment," paper 520 (Houston, TX: NACE International, 1998).

C.J. Nalepa, J.N. Howarth, and R.M. Moore, "A New Single-Feed Liquid Bromine Biocide for Treatment of Cooling Water," Presented at the AWT 1999 Annual Conference, (McLean, VA: Association of Water Technologies, 1999), 17 pages.

Howarth et al., "First Field Trials of Single-Feed, Liquid Bromine Biocide for Cooling Towers", Paper TP00-09 (Houston, Tx.: Cooling Technology Institute, Jan. 31-Feb. 2, 2000), 17 pages.

M. Enzien and B. Yang, "On-line Performance Monitoring of Treatment Programs for MIC Control," paper 01279 (Corrosion 2001, Houston, TX: NACE International, 2001), 13 pages.

Howarth, J.N., et al. "A New, Bromine-Releasing Solid for Microbiological Control of Cooling Water", IWC-01-05, (Pittsburgh, PA: Engineers' Society of Western Pennsylvania, 2001), pp. 1-7.

B.R. Sook, T.F. Ling, and A.D. Harrison "A New Thixotropic Form of Bromochlorodimethylhydantoin: A Case Study," paper 03715 (Corrosion 2003, Houston, TX: NACE International, 2003), pp. 1-16.

C.J. Nalepa, et al., "Strategies for Effective Control of Surface-Associated Microorganisms: A Literature Perspective," IWC-02-01 (Pittsburgh, PA: Engineers' Society of Western Pennsylvania, 2002), 19 pages.

W.G. Characklis and K.C. Marshall, ed., Biofilms: A Basis for an Interdisciplinary Approach, (New York, NY: John Wiley & Sons, 1987), p. 3-5.

J.W. Costerton and P.S. Stewart, "Battling Biofilms," Scientific American (Jul. 2001) 285: 74-81.

M.L. Ludyanskiy and F.J. Himpler, "The Effect of Halogenated Hydantoins on Biofilms," paper 405 (Corrosion 97, Houston, TX: NACE International, 1997), pp. 405/1-405/11.

L.. McNamee, "Efficacy of Hypochlorite vs. Hypobromite in the Removal of a *Pseudomonas aeruginosa* Biofilm," summer intern report (Bozeman, MT: Montana State University, Center for Biofilm Engineering, 2000). pp. 1-23.

C.J. Nalepa, H. Ceri, and C.A. Stremick, "A Novel Technique for Evaluating the Activity of Biocides Against Biofilm Bacteria," paper 00347 (Corrosion 2000, Houston, TX: NACE International, 2000), pp. 00347/1-00347/19.

W.M. Thomas, J. Eccles, and C. Fricker, "Laboratory Observations of Biocide Efficiency against *Legionella* in Model Cooling Tower Systems," paper SE-99-3-4 (Atlanta, GA: ASHRAE Transactions, 1999), pp. 1-17.

"AWT *Legionella* Position Paper: 2003 Update," (McLean, VA: Association of Water Technologies, 2003). pp. 1-33.

"Minimizing the Risk of Legionellosis Associated with Building Water Systems," ASHRAE Guideline 12-2000 (Atlanta, GA: ASHRAE, 2000), 19 pages.

"Legionellosis Guideline: Best Practices for Control of *Legionella*," (Houston, TX: Cooling Tower Institute, Feb. 2000), 8 pages.

Legionellosis: Guidelines for Control of Legionnaires' Disease, (Melbourne, Australia: Health Department Victoria, 1989, (reprinted in 1999), 9 pages.

"Control of *Legionella* in Cooling Towers: Summary Guidelines," (Madison, WI: Wisconsin Division of Health, Aug. 1987), 45 pages.

M.R. Freije, "Legionellae Control in Health Care Facilities: A Guide for Minimizing Risk," (Indianapolis, IN: HC Information Resources, Inc., 1996, pp. 25-41.

Regulatory Advisory, Waterborne Pathogens—Compliance with Joint Commission on Accreditation of Healthcare Organizations Requirements, web address www.ashe.org/media/water.html, visited Jun. 12, 2002, 9 pages.

E. McCall, J.E. Stout, V.L. Yu, and R. Vidic, "Efficacy of Biocides against Biofilm-Associated *Legionella* in a Model System," paper IWC 99-19 (Pittsburgh, PA: Engineers' Society of Western Pennsylvania, 1999), 7 pages.

C.J. Nalepa, et al., "The Activity of Oxidizing Biocides towards *Legionella pneumophila* and the Impact of Biofilms on its Control," paper 01278 (Houston, TX: NACE International, 2001, 21 pages.

C.J. Nalepa, et al., "The Control of Bacteria on Surfaces: Effectiveness of Bromine-Based Biocides towards Microbial Biofilms and Biofilm-Associated *Legionella pneumophila*," paper TP02-13 (Houston, TX: Cooling Technology Institute, 2002), 22 pages.

C.J. Nalepa, et al., "Case Study: A Comparison of Bromine-Based Biocides in a Medium-Size Cooling Tower," paper TP98-09 (Houston, TX: Cooling Tower Institute, 1998), 22 pages.

R. Elsmore, "Development of Bromine Chemistry in Controlling Microbial Growth in Water Systems," International Biodeterioration and Biodegradation (1994) 245-253.

C.J. Nalepa, J.N. Howarth, and F.D. Azamia, "Factors to Consider When Applying Oxidizing Biocides in the Field," paper 02223 (Houston, TX: NACE International, 2002), 20 pages.

Ault et al., "Infrared and Raman Spectra of the M+$Cl_3$ ion Pairs and Their Chlorine-bromine Counterparts isolated in Argon Matrices", Journal of Chemical Physics, 1976, vol. 64, No. 12, pp. 4853-4859.

Willard et al., "Elementary Quantitative Analysis", Third Edition, Chapter XIV, 1933, pp. 261-271.

Summary of Decisions on Miscellaneous and Preliminary Motions, *Yang* v. *Moore*, Interference No. 105,223.

Decision on Moore Preliminary Motion 3, *Yang* v. *Moore*, Interference No. 105,223.

Decision—Interlocatory Motions, *Yang* v. *Moore*, Interference No. 105,223.

Summary of Decisions on Miscellaneous and Preliminary Motions, *Yang* v. *Moore*, Interference No. 105,230.

Decision on Moore Preliminary Motions 2 and 3, *Yang* v. *Moore*, Interference No. 105,230.

Decision—Interlocatory Motions, *Yang* v. *Moore*, Interference No. 105,230.

Summary of Decisions on Miscellaneous and Preliminary Motions, *Yang* v. *Moore*, Interference No. 105,222.

Decision on Moore Preliminary Motions 2 and 3, *Yang* v. *Moore*, Interference No. 105,222.

Decision—Interlocatory Motions, *Yang* v. *Moore*, Interference No. 105,222.

W. Büchner et al., *Industrial Inorganic Chemistry*, p. 180 (1989).

A. A. Frost et al., *Kinetics and Mechanism: A Study of Homogeneous Chemical Reactions*, p. 23 (1953).

M. W. Lister, *Decomposition of Sodium Hypochlorite: The Uncatalyzed Reaction*, pp. 465-478 (1956).

F. A. Cotton et al., *Advanced Inorganic Chemistry*, p. 566 (1999).

J. F. Mills, *The Chemistry of Bromine Chloride in Waste Water Disinfection*, Paper Presented to the American Chemical Society Division of Water, Air, and Waste Chemicals (Aug. 1973).
Dow Chemical Company, *Dow BrCl Newsletter* (Inorganic Chemicals Dept.) (Jul. 1979).
J.F. Mills et al., *Bromine Chloride: An Alternative to Bromine*, Ind. Eng. Chem. Prod. Res. Develop., vol. 12, No. 3, pp. 160-165 (1973).
Z. E. Jolles, *Bromine and its Compounds*, pp. 68, 364, 365 (1966).
Z. E. Jolles, *Bromine and its Compounds*, p. 30 (1966).
Moore's Preliminary Motion No. 1, *Yang v. Moore*, Interference 105,230, filed Dec. 8, 2004.
Moore's Preliminary Motion No. 2, *Yang v. Moore*, Interference 105,230, filed Dec. 8, 2004.
Moore Preliminary Motion No. 3, *Yang v. Moore*, Interference 105,230, filed Dec. 8, 2004.
Moore Preliminary Motion No. 4, *Yang v. Moore*, Interference 105,230, filed Dec. 8, 2004.
Moore Preliminary Motion No. 5, *Yang v. Moore*, Interference 105,230, filed Dec. 8, 2004.
Moore's Preliminary Motion No. 6, *Yang v. Moore*, Interference 105,230, filed Dec. 8, 2004.
Moore Opposition 1 (Prelim Motion 1), *Yang v. Moore*, Interference No. 105,230, filed Feb. 15, 2005.
Yang Alternative Preliminary Motion 1 to Substitute Count, *Yang v. Moore*, Interference No. 105,230, filed Dec. 8, 2004.
Yang Miscellaneous Motion 1 to Vacate Interference No. 105,230 in Favor of Interference No. 105,222, *Yang v. Moore*, Interference No. 105,230, filed Dec. 8, 2004.
Moore Opposition 1 (Miscellaneous Motion 1), *Yang v. Moore*, Interference No. 105,230, filed Feb. 15, 2005.
Yang Opposition to Moore's Preliminary Motion 1, *Yang v. Moore*, Interference No. 105,230, filed Feb. 15, 2005.
Yang Opposition to Moore's Preliminary Motion 2, *Yang v. Moore*, Interference No. 105,230, filed Feb. 15, 2005.
Yang Opposition 3, *Yang v. Moore*, Interference No. 105,230, filed Feb. 15, 2005.
Yang Opposition 4, *Yang v. Moore*, Interference No. 105,230, filed Feb. 15, 2005.
Yang Opposition 5, *Yang v. Moore*, Interference No. 105,230, filed Feb. 15, 2005.
Moore Reply 1, *Yang v. Moore*, Interference No. 105,230, filed Mar. 22, 2005.
Moore Reply 2, *Yang v. Moore*, Interference No. 105,230, filed Mar. 22, 2005.
Moore Reply 3, *Yang v. Moore*, Interference No. 105,230, filed Mar. 22, 2005.
Moore Reply 4, *Yang v. Moore*, Interference No. 105,230, filed Mar. 22, 2005.
Moore Reply 5, *Yang v. Moore*, Interference No. 105,230, filed Mar. 22, 2005.
Yang Reply 1 to Moore's Opposition 1, *Yang v. Moore*, Interference No. 105, 230, filed Mar. 22, 2005.
Yang Reply 1, *Yang v. Moore*, Interference No. 105,230, filed Mar. 22, 2005.
Moore Request for Rehearing of the Decision on Moore Preliminary Motion 2, *Yang v. Moore*, Interference No. 105,230, filed Sep. 27, 2005.
Decision—Rehearing—Bd. R. 125( c) (Including Recommendation to Examiner—Bd. R. 127.(c), *Yang v. Moore*, Interference No. 105,230, Paper 78, filed Jan. 19, 2006.
Judgement—Bd. R. 127, Sep. 29, 2005, *Yang v. Moore*, Interference No. 105,230, Paper 76.
Moore Request for Rehearing of the Judgement, *Yang v. Moore*, Interference No. 105,230, filed Oct. 28, 2005.
Moore Preliminary Motion 1, *Yang v. Moore*, Interference No. 105,223, filed Dec. 8, 2004.
Moore Preliminary Motion 2, *Yang v. Moore*, Interference No. 105,223, filed Dec. 8, 2004.
Moore Preliminary Motion 3, *Yang v. Moore*, Interference No. 105,223, filed Dec. 8, 2004.
Decision—Rehearing—Bd. R.125( c) (Including Recommendation to Examiner—Bd. R. 127( c)), *Yang v. Moore*, Interference No. 105,223, Paper 63, filed Jan. 9, 2006.
Moore Request for Rehearing of the Judgement, *Yang v. Moore*, Interference No. 105,223, filed Oct. 28, 2005.
Judgement—Bd. R. 127, Sep. 29, 2005, *Yang v. Moore*, Interference No. 105,223, Paper 59, filed Sep. 29, 2005.
Moore Request for Rehearing of the Decision on Moore Preliminary Motion 3, *Yang v. Moore*, Interference No. 105,223, filed Sep. 27, 2005.
Moore Exhibit 1106 (Amendment under 37 C.F.R. §1.607, U.S. Appl. No. 09/451,319), *Yang v. Moore*, Interference 105,222, 105,223, and 105,230.
Moore Exhibit 1107 (Moore's Clean Claims), *Yang v. Moore*, Interference 105,222, 105,223, and 105,230, dated Jul. 20, 2004.
Moore Reply 1, *Yang v. Moore*, Interference No. 105,223, filed Mar. 22, 2005.
Moore Reply 2, *Yang v. Moore*, Interference No. 105,223, filed Mar. 22, 2005.
Moore Reply 3, *Yang v. Moore*, Interference No. 105,223, filed Mar. 22, 2005.
Yang Opposition 1, *Yang v. Moore*, Interference No. 105,223, filed Feb. 15, 2005.
Yang Opposition 2, *Yang v. Moore*, Interference No. 105,223, filed Feb. 15, 2005.
Yang Opposition 3, *Yang v. Moore*, Interference No. 105,223, filed Feb. 15, 2005.
Moore Opposition 1 (Prelim. Motion 1), *Yang v. Moore*, Interference No. 105,223, filed Feb. 15, 2005.
Moore Opposition 1 (Misc. Motion 1), *Yang v. Moore*, Interference No. 105,223, filed Feb. 15, 2005.
Yang Alternative Preliminary Motion 1 to Designate Claims as not Corresponding to Count 1, *Yang v. Moore*, Interference No. 105,223, filed Dec. 8, 2004.
Yang Miscellaneous Motion 1 to Vacate Interference No. 105,223 in Favor of Interference No. 105,222, *Yang v. Moore*, Interference No. 105,223, filed Dec. 8, 2004.
Yang Reply 1 to Moore Opposition 1 (Misc. Motion 1), *Yang v. Moore*, Interference No. 105,223, filed Mar. 22, 2005.
Yang Reply 1 to Moore Opposition 1 (Prelim. Motion 1), *Yang v. Moore*, Interference No. 105,223, filed Mar. 22, 2005.
Moore Preliminary Motion 1, *Yang v. Moore*, Interference No. 105,222, filed Dec. 8, 2004.
Moore's Preliminary Motion No. 2, *Yang v. Moore*, Interference No. 105,222, filed Dec. 8, 2004.
Moore Preliminary Motion 3, *Yang v. Moore*, Interference No. 105,222, filed Dec. 8, 2004.
Moore Preliminary Motion 4, *Yang v. Moore*, Interference No. 105,222, filed Dec. 8, 2004.
Moore Preliminary Motion 5, *Yang v. Moore*, Interference No. 105,222, filed Dec. 8, 2004.
Yang Opposition 1, *Yang v. Moore*, Interference No. 105,222, filed Feb. 15, 2005.
Yang Opposition to Moore's Preliminary Motion 2, *Yang v. Moore*, Interference No. 105,222, filed Feb. 15, 2005.
Yang Opposition 3, *Yang v. Moore*, Interference No. 105,222, filed Feb. 15, 2005.
Yang Opposition to Moore's Preliminary Motion 4, *Yang v. Moore*, Interference No. 105,222, filed Feb. 15, 2005.
Yang Opposition 5, *Yang v. Moore*, Interference No. 105,222, filed Feb. 15, 2005.
Yang Opposition 6, *Yang v. Moore*, Interference No. 105,222, filed Feb. 15, 2005.
Yang Miscellaneous Motion 1 to Add Patent Nos. 6,156,229, 6,287,473, 6,123,870 and U.S. Appl. No. 09/785,890 to Interference, *Yang v. Moore*, Interference No. 105,222, filed Dec. 8, 2004.
Yang Alternative Preliminary Motion 2 to Substitute Count, *Yang v. Moore*, Interference No. 105,222, filed Dec. 8, 2004.
Yang Reply 1 (Misc. Motion 1), *Yang v. Moore*, Interference No. 105,222, filed Mar. 22, 2005.
Moore Opposition 1 (Prelim. Motion 1), *Yang v. Moore*, Interference No. 105,222, filed Feb. 15, 2005.
Moore Opposition 1 (Misc. Motion 1), *Yang v. Moore*, Interference No. 105,222, filed Feb. 15, 2005.
Moore Opposition 2, *Yang v. Moore*, Interference No. 105,222, filed Feb. 15, 2005.

Moore Responsive Motion 6, *Yang* v. *Moore*, Interference No. 105,222, filed Jan. 17, 2005.
Judgment—Bd. R. 127, Sep. 29, 2005, *Yang* v. *Moore*, Interference No. 105,222, Paper 67.
Yang Reply 2, *Yang* v. *Moore*, Interference No. 105,222, filed Mar. 22, 2005.
Yang Reply 1 to Moore's Opposition 1, *Yang* v. *Moore*, Interference No. 105,222, filed Mar. 22, 2005.
Yang Preliminary Motion 1 to Designate Claims as not Corresponding to the Count, *Yang* v. *Moore*, Interference No. 105,222, filed Dec. 8, 2004.
Moore Reply 1, *Yang* v. *Moore*, Interference No. 105,222, filed Mar. 22, 2005.
Moore Reply 2, *Yang* v. *Moore*, Interference No. 105,222, filed Mar. 22, 2005.
Moore Reply 3, *Yang* v. *Moore*, Interference No. 105,222, filed Mar. 22, 2005.
Moore Reply 4, *Yang* v. *Moore*, Interference No. 105,222, filed Mar. 22, 2005.
Moore Reply 5, *Yang* v. *Moore*, Interference No. 105,222, filed Mar. 22, 2005.
Moore Reply 6, *Yang* v. *Moore*, Interference No. 105,222, filed Mar. 22, 2005.
Declaration of B. Gary McKinnie, 368047 (Exhibit 1001).
The Second Declaration of B. Gary McKinnie, Feb. 14, 2005 (Exhibit 1073), signed Feb. 14, 2005.
Mills et al., Bromine Chloride: An Alternative to Bromine, Ind. Eng. Chem. Prod. Res. Develop., vol. 12, No. 3, 1973, pp. 160-165 (Exhibit 2014).
Declaration of Dr. Jack Mills, Dec. 6, 2004 (Exhibit 2021), signed Dec. 6, 2004.
Expert Declaration of Dr. Shunong Yang, Dec. 6, 2004 (Exhibit 2022), signed Dec. 6, 2004.
Expert Declaration of John A. Wojtowicz, Dec. 7, 2004 (Exhibit 2023), signed Dec. 7, 2004.
"Chlorination", Betz Handbook of Industrial Water Conditioning, Seventh Edition, pp. 24-29, (Trevose, PA: Betz Laboratories, Inc., 1976).
Cortes CES, et al., "Revisiting the Kinetics and Mechanism of Bromate-Bromide Reaction", J. Braz Chem. Soc., 12(6): pp. 775-779 (2001).
"Current Technology of Chlorine Analysis for Water and Wastewater", (Hach Technical Information Series—Booklet No. 17), (Exhibit 1074).
Excerpts Fleser and Fleser, Introduction to Organic Chemistry, (1957), pp. 192, (Exhibit 1034).
Excerpts from Loudon, C., Organic Chemistry ($2^{nd}$ Edition). Menlo Park, CA: Benjamin/Cummings Publishing Co. (1988), pp. A-11, (Exhibit 1033).

Attached Appendix B of the Expert Declaration of Gary McKinnie (Mathematical Calculations of Ph Values in Goodenough Examples Prior to Bromine Addition), (Exhibit 1019).
Principles of Modern Chemistry (1986), D.W. Oxtobey et al. New York: Saunders College Publishing, pp. 4-7, (Exhibit 1075).
Quantitative Chemical Analysis, $3^{rd}$ ed., D.C. Harris (1991). New York: W.H. Freeman & Co., pp. 181, 195-197, (Exhibit 1079).
Ainstein, V.G. "The General Course of Processes and Apparatuses of Chemical Technology," The Second Book, 2002, pp. 1224-1225, (not translated).
Ainstein, V.G. "The General Course of Processes and Apparatuses of Chemical Technology," The Second Book, 2002, pp. 1307-1308 (not translated).
Ainstein, V.G.; "The General Course in the Processes and Equipment of Chemical Technology"; Book 2; Moscow: 2002; pp. 1224-1225; (3 pages of translation).
Ainstein, V.G.; "The General Course of Processes and Equipment of Chemical Technology"; Book 2; Moscow: 2002; pp. 1307-1308; (3 pages of translation).
"Bromine Chloride for Treating Cooling Water and Wastewater", brochure CD 6-76; Ethyl Corporation, Commercial Development Division; Ferndale, Michigan; 1976; 10 pages.
Farkas and Lewin; "The Dissociation Constant of Hypobromous Acid"; J. Am. Chem. Soc.; 1950; 72; 5766-5767.
"Halogens as Oxidising Agents"; http://www.chemguide.co.uk/inorganic/group7/halogensasoas.html; accessed on Dec. 8, 2008; 8 pages.
Keister et al.; ""Stabilized" Bromine Biocides: Definitions, Chemistry, and Performance", AWT Annual Convention, McLean, VA 2002; 7 pages.
Odeh, ILhab N. et al.; "Kinetics and Mechanisms of Bromine Chloride Reactions with Bromite and Chlorite Ions"; Inorg. Chem.; 2004; 43; 7412-7420.
Tellinghuisen, Joel; "Precise Equilibrium Constants From Spectrophotometric Data: BrCl in Br2/Cl2 Gas Mixtures"; J Phys. Chem. A; 2003; 107; 753-757.
Urtz, Bruce; "Combined Halogens: New Products to Combat an Old Problem" Solutions!, Online Exclusives, Mar. 2003; http://www.tappi.org/Bookstore/Technical-Papers/Journal-Articles/Archive/Solutions/Archives/2003/March/Combined-halogens-new-products-to-combat-an-old-problem-Solutions-Online-Exclusives-March-2003.aspx; accessed on Jul. 20, 2011; 6 pages.
Wang, Tian Xiang et al.; "Equilibrium, Kinetic, and UV-Spectral Characteristics of Aqueous Bromine Chloride, Bromine, and Chlorine Species"; Inorg. Chem.; 1994; 33, 5872-5878.
Becher, D. Z.; "Pesticide Formulations and Application Systems"; ASTM International, 1997, vol. 16, p. 53.

* cited by examiner

ACTIVE BROMINE CONTAINING BIOCIDAL COMPOSITIONS AND THEIR PREPARATION

REFERENCE TO RELATED APPLICATIONS

This application is a continuation-in-part of commonly-owned application Ser. No. 09/506,911, filed Feb. 18, 2000, now U.S. Pat. No. 6,511,682, issued Jan. 28, 2003, which in turn is a continuation-in-part of (1) commonly-owned application Ser. No. 09/404,184, filed Sep. 24, 1999, now U.S. Pat. No. 6,322,822, issued Nov. 27, 2001, and (2) commonly-owned application Ser. No. 09/088,300, filed Jun. 1, 1998, now U.S. Pat. No. 6,068,861, issued May 30, 2000.

This application is also a continuation-in-part of commonly-owned application Ser. No. 09/456,781, filed Dec. 8, 1999, now U.S. Pat. No. 6,495,169, issued Dec. 17, 2002, which in turn is a continuation of commonly-owned application Ser. No. 09/088,300, filed Jun. 1, 1998, now U.S. Pat. No. 6,068,861, issued May 30, 2000.

This application is also a continuation-in-part of commonly-owned copending application Ser. No. 09/451,319, filed Nov. 30, 1999, which in turn is a continuation-in-part of commonly-owned application Ser. No. 09/088,300, filed Jun. 1, 1998, now U.S. Pat. No. 6,068,861, issued May 30, 2000.

This application is also a continuation-in-part of commonly-owned copending application Ser. No. 09/974,622, filed Oct. 9, 2001, now U.S. Pat. No. 6,652,889, issued Nov. 25, 2003, which in turn is a continuation-in-part of commonly-owned application Ser. No. 09/404,184, filed Sep. 24, 1999, now U.S. Pat. No. 6,322,822, issued Nov. 27, 2001, and 09/506,911, filed Feb. 18, 2000, now U.S. Pat. No. 6,511,682, issued Jan. 28, 2003, both of which are continuations-in-part of commonly-owned application Ser. No. 09/088,300, filed Jun. 1, 1998, now U.S. Pat. No. 6,068,861, issued May 30, 2000. Said application Ser. No. 09/506,911 is also a continuation-in-part of said application Ser. No. 09/404,184.

The disclosures of each of commonly-owned copending application Ser. Nos. 09/506,911, filed Feb. 18, 2000; 09/456,781, filed Dec. 8, 1999; 09/451,319, filed Nov. 30, 1999; and Ser. No. 09/974,622, filed Oct. 9, 2001 are incorporated herein by reference as if fully set forth herein. The Issue Fees have been paid in each of application Ser. Nos. 09/506,911, filed Feb. 18, 2000; and Ser. No. 09/456,781, filed Dec. 8, 1999.

REFERENCE TO OTHER COMMONLY-OWNED APPLICATIONS

Other commonly-owned U.S. applications and patents relating to similar subject matter, or which may be considered to relate to similar subject matter, include the following:

Ser. No. 09/296,499, filed Apr. 22, 1999, now U.S. Pat. No. 6,110,387, issued Aug. 29, 2000
Ser. No. 09/442,025, filed Nov. 17, 1999, now U.S. Pat. No. 6,306,441, issued Oct. 23, 2001
Ser. No. 09/451,344, filed Nov. 30, 1999, now U.S. Pat. No. 6,352,725, issued Mar. 5, 2002
Ser. No. 09/658,839, filed Sep. 8, 2000, now U.S. Pat. No. 6,375,991, issued Apr. 23, 2002
Ser. No. 09/663,788, filed Sep. 18, 2000, now U.S. Pat. No. 6,348,219, issued Feb. 19, 2002
Ser. No. 09/663,948, filed Sep. 18, 2000, now U.S. Pat. No. 6,299,909, issued Oct. 9, 2001
Ser. No. 09/732,601, filed Dec. 7, 2000, now U.S. Pat. No. 6,506,418, issued Jan. 14, 2003
Ser. No. 09/785,890, filed Feb. 16, 2001,
Ser. No. 10/120,334, filed Apr. 10, 2002, now U.S. Pat. No. 6,551,624, issued Apr. 22, 2003
Ser. No. 10/269,901, filed Oct. 10, 2002, now U.S. Pat. No. 7,195,782, issued Mar. 27, 2007.

The disclosures of the above U.S. Patents are incorporated herein by reference as if fully set forth herein.

BACKGROUND

Bromine-based biocides have proven biocidal advantages over chlorination-dechlorination for the microbiological control of cooling waters and disinfection of waste treatment systems. The water treatment industry recognizes these advantages to be cost-effective control at higher pH values, almost no loss in biocidal activity in the presence of ammonia, and effective control of bacteria, algae and mollusks.

A common way of introducing bromine based biocides into a water system is through the use of aqueous NaBr in conjunction with NaOCl bleach. The user feeds both materials to a common point whereupon the NaOCl oxidizes the bromide ion to $HOBr/OBr^{\ominus}$. This activated solution is then introduced directly into the water system to be treated. The feeding of the two liquids in this fashion is necessary because the $HOBr/OBr^{\ominus}$ mixture is unstable and has to be generated on-site just prior to its introduction to the water. Furthermore, the feeding and metering of two liquids is cumbersome, especially as the system has to be designed to allow time for the activation of bromide ion to occur. Consequently, many biocide users have expressed the need for a single-feed, bromine-based biocide. Elemental bromine and molecular bromine chloride have been considered to meet these demands. Both are liquids at room temperature and can be fed directly to the water system, where immediate hydrolysis occurs to yield HOBr.

$$Br_2 + H_2O \rightarrow HOBr + HBr \quad (1)$$

$$BrCl + H_2O \rightarrow HOBr + HCl \quad (2)$$

Properties of bromine and bromine chloride are compared in Table 1.

TABLE 1

Physical Properties of Bromine and Bromine Chloride

| Property | Bromine ($Br_2$) | Bromine Chloride (BrCl) |
|---|---|---|
| Appearance | Fuming, dark-red liquid | Fuming, red liquid or gas |
| Boiling Point | 59° C. | 5° C. |
| Vapor Pressure (25° C.) | 214 mm | 1800 mm |
| Corrosivity | Corrodes most metals in the presence of water | Corrodes most metals in the presence of water |

It can be seen that certain characteristics of these materials—especially their corrosiveness, high vapor pressures and fuming tendencies—necessitate care and skill in their handling and use. Early efforts to overcome the deficiencies of this material comprised complexing bromine with excess bromide ion in the presence of strong acid and stabilizing the resultant solutions with ethanolamine. The resultant solutions of ethanolammonium hydrogen perbromide contained up to 38% by weight elemental bromine. See in this connection, Favstritsky, U.S. Pat. No. 4,886,915; and Favstritsky, Hein, and Squires, U.S. Pat. No. 4,966,716.

These solutions permitted introduction of bromine to a water system using a single feed. As in the case of bromine and bromine chloride, the ethanolammonium hydrogen perbromide hydrolyzed in water to release HOBr. The vapor pressures of these solutions were lower than elemental bromine and bromine chloride. Nevertheless, the solutions still possessed measurable vapor pressures, and thus tended to produce undesirable reddish-colored vapors during storage and use.

An economically acceptable way of stabilizing high concentrations of aqueous solutions of bromine chloride is described in U.S. Pat. No. 5,141,652 to Moore, et al. The solution is prepared from bromine chloride, water and a halide salt or hydrohalic acid. These solutions were found to decompose at a rate of less than 30% per year and in cases of high halide salt concentration, less than 5% per year. Moreover, solutions containing the equivalent of 15% elemental bromine could be prepared. Unfortunately, the relatively high acidity of these solutions and their tendency to be corrosive and fuming impose limitations on their commercial acceptance.

Many solid bromine derivatives such as BCDMH (1,3-bromochloro-5,5-dimethylhydantoin) are limited in the amount of material that can be dissolved in water and fed as a liquid to the water treatment system. For example, the solubility of BCDMH in water is only around 0.15%. Another limitation of such derivatives is that at neutral pH, HOBr rapidly decomposes, eventually forming bromide ions. Thus, the ability to store and transport these aqueous solutions is greatly limited and of questionable commercial feasibility.

U.S. Pat. No. 3,558,503 to Goodenough et al. describes certain aqueous bromine solutions stabilized with various stabilizing agents and various uses to which such solutions can be put. The compositions described in the patent comprise an aqueous bromine solution having from about 0.01 to about 100,000 parts per million by weight of bromine values wherein the molar ratio of bromine to nitrogen present in the bromine stabilizer ranges from about 2.0 to 1 to about 0.5 to 1. The stabilizer used is biuret, succinimide, urea, a lower aliphatic mono- or disubstituted urea containing from about 2 to about 4 carbon atoms in each substituent group, sulfamic acid, or an alkyl sulfonamide of the formula $RSO_3NH_2$ where R is a methyl or ethyl group. The solution also contains sufficient hydroxide additive to provide a pH in the solution ranging from about 8 to about 10, the hydroxide additive being an alkaline earth hydroxide or an alkali metal hydroxide.

U.S. Pat. No. 5,683,654 to Dallmier et al. discusses the preparation of aqueous alkali metal or alkaline earth metal hypobromite solutions by mixing an aqueous solution of alkali or alkaline earth metal hypochlorite with a water soluble bromide ion source to form a solution of unstabilized alkali or alkaline earth metal hypochlorite. To this solution is added an aqueous solution of an alkali metal sulfamate having a temperature of at least 50° C. and in an amount that provides a molar ratio of alkali metal sulfamate to alkali or alkaline earth metal hypobromite of from about 0.5 to about 6 whereby a stabilized aqueous alkali or alkaline earth metal hypobromite solution is formed. The Dallmier et al. patent teaches that much higher levels of available halogen for disinfection were attained by this approach as compared to the Goodenough et al. approach. But the Dallmier et al. patent acknowledges that in their process, the stabilization must occur quickly after the unstable NaOBr is formed.

Thus, there is a need for a water-soluble bromine-based biocide that is non-acidic and noncorrosive. There also remains a need for methods of disinfecting surfaces and of sanitizing bodies of water using a single-feed, bromine-based biocide that is water-soluble, non-acidic, and noncorrosive.

THE INVENTION

This invention provides, among other things, highly concentrated aqueous active bromine-containing biocidal solutions which have surprisingly high storage stability, higher even than present commercially-available more dilute aqueous biocidal solutions formed from the same components and thus presumably having the same or very similar chemical composition except for concentration. This invention further involves, among other things, new, highly water-soluble solid state bromine-containing biocidal compositions which are suitable for storage and shipment in the solid state and which can be used either as an effective biocidal additive for direct addition in the form of solids to industrial or recreational water systems or as the raw material for the formation of highly active aqueous biocidal solutions or slurries of any desired concentration for addition to industrial or recreational water systems. Thus this invention makes it possible to reduce storage space and shipping costs associated with the manufacture and transport of highly effective active bromine-containing biocidal compositions. In other words, by providing either more highly concentrated aqueous solutions of the biocide or the biocide itself in solid form, the storage space, shipping volumes, and shipping costs of the biocidal products of this invention can be significantly reduced. Moreover, the desirable storage stability of the solid state biocidal products of this invention and the surprising increased storage stability of more highly concentrated solutions of this invention as compared to more dilute commercially-available solutions are still further advantages of this invention. It has also been found that more highly concentrated biocidal compositions of this invention surprisingly can have either equal or lower crystallization temperatures than a more dilute commercially-available composition made from the same components.

Also provided by this invention are processes of forming the new highly concentrated aqueous active bromine-containing biocidal solutions or slurries of this invention and processes of forming the new solid state biocidal products of this invention.

Preferred highly concentrated aqueous active bromine compositions of this invention are solids-free aqueous solutions in which the content of active bromine is greater than about 160,000 ppm. In other words, the active bromine in these preferred liquid biocides is all in solution at room temperature (e.g., 23° C.).

An embodiment of this invention is an aqueous biocide composition comprising water having in solution therein (i) an active bromine content derived from bromine chloride of greater than about 160,000 ppm (wt/wt), and (ii) an overbased alkali metal salt of sulfamic acid (most preferably a sodium salt), and optionally containing—but preferably containing—(iii) an alkali metal halide (preferably sodium chloride or sodium bromide, or both), wherein the relative proportions of (i) and (ii) are such that the atom ratio of nitrogen to active bromine is greater than 0.93, and preferably is greater than 1 (e.g., in the range of above 1 to about 1.5) and wherein the pH of the composition is at least 7 (e.g., in the range of 10 to about 13.5, and preferably in the range of about 12.5 to about 13.5, or even as high as about 14). The content of active bromine in the solution is typically in the range of above about 160,000 ppm to about 215,000 ppm. Preferably, the content of active bromine in the concentrated liquid biocidal solutions of this invention (whether formed from use of (a) BrCl, or (b) $Br_2$, or (c) BrCl and $Br_2$, or (d) $Br_2$ and $Cl_2$), or (e) BrCl, $Br_2$ and $Cl_2$), is in the range of about 165,000 ppm (wt/wt) to about 215,000 ppm (wt/wt), more preferably in the range of about 170,000 ppm (wt/wt) to about 215,000 ppm (wt/wt), and still more preferably in the range of about 176,000 ppm (wt/wt) to about 215,000 ppm (wt/wt).

In one particularly preferred embodiment the content of active bromine in the concentrated liquid biocidal compositions of this invention (whether formed from use of (a) BrCl, or (b) $Br_2$, or (c) BrCl and $Br_2$, or (d) $Br_2$ and $Cl_2$, or (e) BrCl, $Br_2$ and $Cl_2$) is in the range of about 176,000 ppm to about 190,000 ppm (wt/wt).

In another particularly preferred embodiment the content of active bromine in the liquid biocidal compositions of this invention (whether formed from use of (a) BrCl, or (b) $Br_2$, or (c) BrCl and $Br_2$, or (d) $Br_2$ and $Cl_2$, or (e) BrCl, $Br_2$ and $Cl_2$) is in the range of from about 201,000 ppm to about 215,000 ppm.

It is also preferred, to provide in the product an atom ratio of nitrogen to active bromine from (i) and (ii) that is greater than 1 even when using bromine chloride in forming the product. In another preferred embodiment the overbased aqueous solution of alkali metal salt of sulfamic acid used in the process is preformed by mixing together in water, (1) sulfamic acid and/or an alkali metal salt of sulfamic acid, and (2) alkali metal base in proportions such that during the reaction with one of the above-specified sources of active bromine, the feed of the aqueous solution of alkali metal salt of sulfamic acid keeps the aqueous reaction solution at a pH of at least 7, e.g., in the range of 10 to about 12 or 12.5, and preferably in the range of about 12.5 to about 13.5. If sulfamic acid itself is used as the starting material, it is used initially as a slurry in water with which the alkali metal base is mixed. The alkali metal base can be cofed along with sulfamic acid or alkali metal sulfamate, if desired.

Although any of (a) BrCl, or (b) $Br_2$, or (c) BrCl and $Br_2$, or (d) $Br_2$ and $Cl_2$, or (e) BrCl, $Br_2$ and $Cl_2$ can be used as the source of the active bromine in the compositions of this invention, it is preferred to use either bromine chloride or a mixture of bromine chloride and bromine, especially where the mole ratio of BrCl to $Br_2$ used is greater than 1, as these provide a product of very desirable properties, and enable highly efficient plant operation and relatively low plant investment costs.

In one of its embodiments this invention provides a concentrated liquid biocide composition which comprises an aqueous solution of active bromine formed from (a) bromine, bromine chloride or a mixture of bromine chloride and bromine with (b) an overbased aqueous solution of alkali metal salt of sulfamic acid (preferably the sodium salt), the solution having a pH of at least about 7, e.g., in the range of about 10 to about 13.5, and preferably in the range of about 12.5 to about 13.5. The amounts of (a) and (b) used are such that (i) the content of active bromine in the concentrated solution is in the range of above about 160,000 ppm (wt/wt) to about 215,000 ppm (wt/wt) (ii) the atom ratio of nitrogen to active bromine from (a) and (b) is greater than 1 when bromine is used (i.e., without bromine chloride), and greater than 0.93 when bromine chloride is used (i.e., with or without bromine). In a preferred embodiment the content of active bromine in the concentrated liquid biocidal solution is in the range of from about 165,000 ppm (more preferably about 176,000 ppm) to about 215,000 ppm (wt/wt). In one particularly preferred embodiment the content of active bromine in the concentrated liquid biocidal solution is in the range of from about 176,000 ppm to about 190,000 ppm (wt/wt). In another particularly preferred embodiment the content of active bromine in the concentrated liquid biocidal solution is in the range of from about 201,000 ppm to about 215,000 ppm. It is also preferred, to utilize an atom ratio of nitrogen to active bromine from (a) and (b) that is greater than 1 even when using bromine chloride in forming the product. In another preferred embodiment the aqueous solution of alkali metal salt of sulfamic acid used in the process is preformed by mixing together in water, (i) sulfamic acid and/or an alkali metal salt of sulfamic acid, and (ii) alkali metal base in proportions such that an aqueous solution of alkali metal salt of sulfamic acid is formed having a pH of at least 7, e.g., in the range of 10 to about 12 or 12.5, and preferably in the range of about 12.5 to about 13.5 or 14. If sulfamic acid itself is used as the starting material, it is used initially as a slurry in water with which the alkali metal base is mixed.

In one of its embodiments this invention provides a process of producing a concentrated liquid biocide composition which comprises mixing (a) bromine with (b) an overbased aqueous alkaline solution of alkali metal salt of sulfamic acid (preferably the sodium salt), the solution having a pH of at least about 7, typically at least about 10, desirably at least about 12, e.g., in the range of about 12 to about 14, and preferably in the range of 12 to about 13.5 or 14. The amounts of (a) and (b) used are such that (i) the content of active bromine in the solution is as described above and (ii) the atom ratio of nitrogen to active bromine from (a) and (b) is greater than 1. In a preferred embodiment, the aqueous solution of alkali metal salt of sulfamic acid used in the process is preformed by mixing together in water, (i) sulfamic acid and/or an alkali metal salt of sulfamic acid, and (ii) alkali metal base in proportions such that an aqueous solution of alkali metal salt of sulfamic acid is formed having a pH of at least 12. If sulfamic acid itself is used as the starting material, it is used initially as a slurry in water with which the alkali metal base is mixed.

Also provided by this invention is a solid state bromine-containing biocidal composition formed by removal of water from an aqueous solution or slurry of a product formed in water from (A) (i) bromine, (ii) bromine chloride, (iii) a mixture of bromine chloride and bromine, (iv) bromine and chlorine in a $Br_2$ to $Cl_2$ molar ratio of at least about 1, or (v) bromine chloride, bromine, and chlorine in proportions such that the total $Br_2$ to $Cl_2$ molar ratio is at least about 1; and (B) (i) alkali metal salt of sulfamic acid and/or sulfamic acid, and (ii) alkali metal base, wherein said aqueous solution or slurry has a pH of at least 7 and an atom ratio of nitrogen to active bromine from (A) and (B) of greater than 0.93. The concentration of the product formed in water from (A) and (B) used in forming the solid state bromine-containing biocidal composition is not critical; any concentration can be present in the initial aqueous solution or slurry. Naturally it is desirable to start with a more concentrated solution or slurry as this lessens the amount of water that must be removed when preparing the solid state bromine-containing biocidal composition.

The solid state bromine-containing biocidal compositions of this invention are preferably formed by spray drying the aqueous solution or slurry of the product formed from (A) and (B). Temperatures of the atmosphere (e.g., dry air or nitrogen) into which the spray is directed is typically in the range of about 20 to about 100° C., and preferably is in the range of about 20 to about 60° C., particularly when the process is carried out at reduced pressure. When spray drying is used it is preferred to use the product formed from (A) and (B) as a solution rather than as a slurry as this minimizes the possibility of nozzle pluggage. On the other hand, if the water is to be flashed off or otherwise distilled from the solution or slurry of the product formed from (A) and (B), it is preferred to use the product formed from (A) and (B) as a slurry rather than as a solution as this minimizes the amount of water to be removed. Such flashing or distillations can be, and preferably are, conducted at reduced pressures to reduce the temperatures to which the product formed from (A) and (B) is exposed during drying.

The solid state bromine-containing biocidal compositions of this invention are typically in the form of powders or relatively small particles. However the solid state bromine-containing biocidal compositions of this invention can be compacted into larger forms such as nuggets, granules, pellets, tablets, pucks, and the like, by use of known procedures. Such compacted products may be formed with the use of binding agents or other materials that cause the particles to adhere one to another. If the binder used is not readily soluble in water, it is important not to totally encapsulate the product with a water-impervious coating of such binder that remains intact under actual use conditions, as this would prevent contact between the encapsulated bromine-containing biocidal composition and the water being treated with the biocidal composition. Low melting waxes or the like may be used to bind and even to encapsulate the bromine-containing biocidal composition in cases where the encapsulated product is used in waters at high enough temperatures to melt off the coating and bindings so that the water can come into contact with the previously encased biocidal composition itself. However, use of binding substances that are water-soluble or that provide effective binding action in proportions insufficient to encapsulate the particles being bound together, is preferable. The binding agent used should be compatable with the solid state bromine-containing biocidal composition of this invention.

Another embodiment of this invention is a method of disinfecting a surface having biofilm thereon, which method comprises introducing into water in contact with said biofilm or that comes in contact with said biofilm a biocidally effective amount of a concentrated aqueous biocidal solution or slurry formed from bromine chloride and an overbased aqueous solution of an alkali metal salt of sulfamic acid (preferably the sodium salt), such composition having an active bromine content greater than about 160,000 ppm (wt/wt), a pH of at least about 7 (e.g., in the range of 7 to about 13.5 or even 14, typically in the range of 10 to about 13.5, and preferably in the range of about 12.5 to about 13.5) and an atom ratio of nitrogen to active bromine of greater than 0.93, and preferably greater than 1. This atom ratio of course is based on the amounts of bromine chloride and alkali metal sulfamate used in forming the concentrated aqueous biocidal solution or slurry. The water being treated pursuant to this embodiment may contain, and typically will contain, planktonic bacteria, and the biocidally effective amount of the concentrated aqueous biocidal solution or slurry added to the water should be sufficient to control such bacteria as well as the biofilm. In this embodiment it is preferred to use a concentrated aqueous biocidal solution solids-free aqueous solution in which the content of active bromine is greater than about 160,000 ppm, however slurries are also effective. The content of active bromine in the solution is typically in the range of above about 160,000 ppm to about 215,000 ppm. Preferably, the content of active bromine in the concentrated liquid biocidal solutions used in this embodiment (whether the active bromine is formed from use of (a) BrCl, or (b) $Br_2$, or (c) BrCl and $Br_2$, or (d) $Br_2$ and $Cl_2$, or (e) BrCl, $Br_2$ and $Cl_2$), is in the range of about 165,000 ppm (wt/wt) to about 215,000 ppm (wt/wt), more preferably in the range of about 170,000 ppm (wt/wt) to about 215,000 ppm (wt/wt), and still more preferably in the range of about 176,000 ppm (wt/wt) to about 215,000 ppm (wt/wt). In one particularly preferred embodiment the content of active bromine in the concentrated liquid biocidal composition used in the control of biofilm (whether the active bromine is formed from use of (a) BrCl, or (b) $Br_2$, or (c) BrCl and $Br_2$, or (d) $Br_2$ and $Cl_2$, or (e) BrCl, $Br_2$ and $Cl_2$) is in the range of about 176,000 ppm to about 190,000 ppm (wt/wt). In another such particularly preferred embodiment the content of active bromine in the liquid biocidal composition used (whether formed from use of (a) BrCl, or (b) $Br_2$, or (c) BrCl and $Br_2$, or (d) $Br_2$ and $Cl_2$, or (e) BrCl, $Br_2$ and $Cl_2$) is in the range of from about 201,000 ppm to about 215,000 ppm.

Still another embodiment of this invention is a method of disinfecting a body of water such as a body of recreational water, a body of industrial water, a body of wastewater, or a body of process water, which method comprises introducing into such water a biocidally effective amount of a concentrated aqueous biocidal solution or slurry described in the immediately preceding paragraph.

Yet another embodiment of this invention is a method of disinfecting a surface having biofilm thereon, which method comprises introducing into water in contact with said biofilm or that comes in contact with said biofilm a biocidally effective amount of a solid state bromine-containing biocidal composition of this invention. It will be recalled that such solid state compositions are formed by removal of water from an aqueous solution or slurry of a product formed in water from (A) (i) bromine, (ii) bromine chloride, (iii) a mixture of bromine chloride and bromine, (iv) bromine and chlorine in a $Br_2$ to $Cl_2$ molar ratio of at least about 1, or (v) bromine chloride, bromine, and chlorine in proportions such that the total $Br_2$ to $Cl_2$ molar ratio is at least about 1; and (B) (i) alkali metal salt of sulfamic acid and/or sulfamic acid, and (ii) alkali metal base, wherein said aqueous solution or slurry has a pH of at least 7 and an atom ratio of nitrogen to active bromine from (A) and (B) of greater than 0.93. The concentration of the product formed in water from (A) and (B) used in forming the solid state bromine-containing biocidal composition is not critical; any concentration can be present in the initial aqueous solution or slurry. Naturally it is desirable to start with a more concentrated solution or slurry as this lessens the amount of water that must be removed when preparing the solid state bromine-containing biocidal composition. The water being treated pursuant to this embodiment may contain, and typically will contain, planktonic bacteria, and the biocidally effective amount of the concentrated aqueous biocidal solution or slurry added to the water should be sufficient to control such bacteria as well as the biofilm.

Still another embodiment of this invention is a method of disinfecting a body of water such as a body of recreational water, a body of industrial water, a body of wastewater, or a body of process water, which method comprises introducing into such water a biocidally effective amount of a solid state bromine-containing biocidal composition of this invention such as described, for example, in the immediately preceding paragraph. In a preferred embodiment the water being treated is in a subterranean well being serviced or is in a subterranean hole being drilled in connection with oilfield or gasfield operations. In such treatments the solid state bromine-containing biocidal composition of this invention is readily introduced into the subterranean water by gravity and is highly effective for killing not only common biofilm and planktonic organisms in general, but sessile bacteria as well, thus prevention the well from going sour. It is also possible to employ a biocidally effective amount of a concentrated aqueous biocidal solution or slurry of this invention in carrying out the methods described in this paragraph, and thus methods of this type using such a concentrated aqueous biocidal solution or slurry constitute still additional embodiments of this invention.

In all of the embodiments of this invention, the alkali metal content of the alkali metal salts of sulfamic acid and of the alkali metal bases used in forming the compositions of this invention is preferably potassium and more preferably is sodium.

The above and other embodiments of this invention will be still further apparent from the ensuing description and appended claims.

FURTHER DETAILED DESCRIPTION

When introducing the bromine source, e.g., bromine chloride or bromine into the aqueous solution of alkali metal salt of sulfamic acid, it is desirable to maintain the desired pH of the resulting solution at 7 or above by also introducing into the solution (continuously or intermittently, as desired) additional alkali metal base, such as by a co-feed of an aqueous solution of alkali metal base. When the concentrated aqueous solution is to be stored in drums, it is desirable to have the pH of such solution at about 10 or above, and preferably in the range of about 12.5 to about 13.5. The pH can be as high as 14 if desired.

It is preferred to employ bromine chloride (or a mixture of bromine chloride and bromine in which less than 50 mole % of the mixture is bromine) as the source of the active bromine in the above process because in the resulting aqueous compositions, all of the bromine of the bromine chloride is made available as active bromine capable of providing biocidal activity in solution. In other words, the chlorine of the bromine chloride is converted in the process to dissolved alkali metal chloride salt, thereby liberating the bromine as the active bromine content of the biocidal composition which is capable of providing biocidal activity. Thus the more expensive component of the bromine chloride—viz., bromine—is fully utilized in forming active bromine in the aqueous biocidal composition, and concurrently the less expensive component—the anionic chlorine in the bromine chloride—makes this beneficial result possible.

A general procedure for preparing the compositions of this invention using sulfamic acid involves, as a first step, forming a slurry of sulfamic acid in water. Typically the pH of this slurry is below 1 pH unit. Sodium hydroxide at 50% concentration is then added until the solid is completely dissolved. Additional 50% NaOH is added until the desired pH is reached. The source of bromine, such as bromine or bromine chloride is then added at a rate to allow the bromine to dissolve and react with the sulfamic acid without forming a pool of halogen on the bottom of the reactor. On a laboratory scale, a convenient rate of addition is approximately two drops per second. Sodium hydroxide (e.g., 25% or 50%) is co-fed to the reactor to maintain the desired pH (e.g., in the range of 7 to about 13.5, and it is possible to operate even at a pH in the range of 13.5 to 14. It has been found that stable solutions containing as much as 26% active bromine (11.5% on an active chlorine basis) can be prepared by the process of this invention. While solutions containing as much as 26% active bromine (i.e., 260,000 ppm wt/wt) were stable enough for use in contemporaneous laboratory experiments, for commercial purposes where product must be stored and shipped for use offsite, compositions containing in the range of above about 160,000 ppm (wt/wt) to about 215,000 ppm (wt/wt) of active bromine not only have superior stability as compared to compositions containing amounts of active bromine significantly above this range, but in addition have superior stability as compared to compositions containing amounts of active bromine significantly below this range.

The term "active bromine" of course refers to all bromine-containing species that are capable of biocidal activity. It is generally accepted in the art that all of the bromine in the +1 oxidation state is biocidally active and is thus included in the term "active bromine". As is well known in the art, bromine, bromine chloride, hypobromous acid, hypobromite ion, hydrogen tribromide, tribromide ion, and organo-N-brominated compounds have bromine in the +1 oxidation state. Thus these, as well as other such species to the extent they are present, constitute the active bromine content of the compositions of this invention. See, for example, U.S. Pat. No. 4,382,799 and U.S. Pat. No. 5,679,239. A well-established method in the art for determining the amount of active bromine in a solution is starch-iodine titration, which determines all of the active bromine in a sample, regardless of what species may constitute the active bromine. The usefulness and accuracy of the classical starch-iodine method for quantitative determination of bromine and many other oxidizing agents has long been known, as witness Chapter XIV of Willard-Furman, *Elementary Quantitative Analysis*, Third Edition, D. Van Nostrand Company, Inc., New York, Copyright 1933, 1935, 1940.

A typical starch-iodine titration to determine active bromine is carried out as follows: A magnetic stirrer and 50 milliliters of glacial acetic acid are placed in an iodine flask. The sample (usually about 0.2-0.5 g) for which the active bromine is to be determined is weighed and added to the flask containing the acetic acid. Water (50 milliliters) and aqueous potassium iodide (15% (wt/wt); 25 milliliters) are then added to the flask. The flask is stoppered using a water seal. The solution is then stirred for fifteen minutes, after which the flask is unstoppered and the stopper and seal area are rinsed into the flask with water. An automatic buret (Metrohm Limited) is filled with 0.1 normal sodium thiosulfate. The solution in the iodine flask is titrated with the 0.1 normal sodium thiosulfate; when a faint yellow color is observed, one milliliter of a 1 wt % starch solution in water is added, changing the color of the solution in the flask from faint yellow to blue. Titration with sodium thiosulfate continues until the blue color disappears. The amount of active bromine is calculated using the weight of the sample and the volume of sodium thiosulfate solution titrated. Thus, the amount of active bromine in a composition of this invention, regardless of actual chemical form, can be quantitatively determined.

By utilizing bromine or bromine chloride with caustic in the stabilized bromine composition, higher levels of active halogen are achievable, compared to the levels obtained by the addition of sodium hypochlorite to sodium bromide. The process and the compositions formed also have about twice the content of active bromine as the most concentrated solutions produced pursuant to the above Goodenough, et al. patent. Moreover, even at high levels of active bromine, it has been found possible to provide biocidal compositions that maintain these high levels of active bromine for at least a two-month period, and that do not exhibit a visible or offensive vapor or odor during this period.

It has been found that highly concentrated aqueous active bromine-containing biocidal solutions of this invention have surprisingly high storage stability, higher even than present commercially-available more dilute aqueous biocidal concentrates formed from the same components and thus presumably having the same or similar composition except for concentration. For example, samples of higher active bromine concentration than those currently marketed by Albemarle Corporation were prepared by obtaining a commercial sample of Stabrom™ 909 biocide (Albemarle Corporation), removing water therefrom under vacuum, and determining properties of the resultant products. Details of this experimental work are set forth in the following illustrative examples.

EXAMPLE 1

A 1000 mL round-bottom flask fitted with a thermometer, water condenser, and water bath was charged with 800 g Stabrom 909 biocide. The active bromine content of this original commercial sample was 14.82% as determined by the KI/thiosulfate method. In other words this sample of commercial product had an active bromine content of 148,200 ppm (wt/wt). The water bath was heated with a magnetic stirrer/heater and a 28 mm vacuum was applied on the apparatus. Water distilled over at 29-32° C. at a bath temperature of 48-57° C. The distillation was stopped after 45 minutes. The amount of product remaining in the distillation flask was 668 g. Analysis by the KI/thiosulfate method indicated an activity of 17.87% as active bromine. In other words, the analysis indicated that the active bromine content of this partially dewatered composition was 178,700 ppm (wt/wt).

EXAMPLE 2

The procedure of Example 1 was followed. The round-bottom flask was charged with 1000 g Stabrom 909 biocide. Water distilled over from 31-33° C. at a bath temperature of 42-55° C. The distillation was stopped after 2½ hours. The amount of product remaining in the distillation flask was 692 g. Analysis of this partially dewatered product by the KI/thiosulfate method indicated an activity of 21.19% as active bromine, i.e., the indicated active bromine content of this composition was 211,900 ppm (wt/wt).

EXAMPLE 3

The stabilities of the highly concentrated compositions of this invention formed in Example 1 and 2 were compared to the stability of the more dilute starting sample. A sample of the product of Example 1 was poured into one 8 oz. wide-mouth polyethylene bottle, a sample of the product of Example 2 was poured into another 8 oz. wide-mouth polyethylene bottle, and a sample of the original more dilute Stabrom 909 biocide concentrate was poured into a third 8 oz. wide-mouth polyethylene bottle. Each bottle was filled to about ½ of its total volume. The bottles were loosely capped and placed in a recirculating air oven maintained at 45° C. The samples were periodically removed and analyzed for activity (i.e., content of active bromine). Table 2 summarizes the data. The ½-life data shown in Table 2 is calculated from the slope of the least squares line obtained by plotting the data in the form of ln(activity at time=t)/(activity at time=0) vs. time. This represents a first order kinetic analysis of the data. For further information on this technique, reference may be made to Arthur Adamson, *A Textbook of physical Chemistry*, pp. 617-620, Academic Press, NY, 1973. The data from these experiments indicate that the samples obtained from Example 1 and Example 2 have excellent storage stability with half-lives exceeding that of the commercial material. Thus even though more concentrated, the compositions of this invention had even greater stability than the less concentrated commercial composition.

In Table 2, the values shown for Control (Stabrom 909 biocide) and the compositions of Example 1 and Example 2 are in terms of wt % of active bromine. Thus a value of 14.86 wt % is equivalent to 148,600 ppm (wt/wt).

TABLE 2

| Days at 45° C. | Control, wt % | Example 1, wt % | Example 2, wt % |
|---|---|---|---|
| 0 | 14.86 | 17.81 | 21.25 |
| 7 | — | — | 20.87 |
| 8 | 14.5 | 17.48 | — |
| 14 | — | — | 20.46 |
| 23 | 14.02 | 16.95 | — |
| 28 | — | — | 19.74 |
| 42 | 13.23 | 16.29 | 19.09 |
| ½-Life (days) | 254 | 328 | 272 |

EXAMPLE 4

The crystallization temperatures of the high activity active bromine samples of Examples 1 and 2 were compared to the starting sample (Control). In general, the procedure used was as follows: A glass tube containing 30 mL of sample is mechanically stirred while being cooled. At 10° C. above the expected freezing point temperature, the sample is cooled at a rate of approximately 0.5° C./min. until the formation of crystals are observed. The temperatures are recorded for 10 minutes after crystals have formed. A pour point tube containing sample is placed into an ethylene glycol bath. The sample stays at one temperature for eight hours. The bath temperature will be lowered by ten degrees if the sample does not freeze. The test continues until the sample freezes.

More specifically, the steps used in the procedure are as follows:

1) Measure approximately 30 mL of sample into the jacketed glass tube.
2) Add 0.03 g of crushed glass as a seeding material to the sample.
3) Insert the rubber stopper/thermometer/helical stirrer assembly in the sample. (The tip of the probe should be positioned about half an inch from the bottom of the tube).
4) Support the tubes in the cooling bath until the level of the sample and acetone are approximately equal.
5) Secure the second temperature probe in the acetone bath so it is not touching the bottom or sides.
6) Start stirring the sample, slowly and carefully begin adding dry ice to the acetone bath. Keep the stirrer in the sample while stirring. Avoid taking the stirrer out of the sample. This will cause air bubbles to form in the sample.
7) Watch the temperature begin to decrease on the thermometer display. The temperature of the sample in the tube will decrease at a fairly steady rate. At approximately 10° C. above the expected freezing point, the cooling rate should be maintained at about 0.5° C./min.
8) Continue cooling and monitoring the temperature. When all the sample has crystallized monitor the sample. The freezing point temperature should stabilize briefly (10-20 seconds). If supercooling is evident, the freezing point temperature will be taken where the temperature levels off after the temperature rise. If the sample does not crystallize at −46° C., the test is stopped.
9) Check to see if crystals go back into solution after the sample has warmed to room temperature.

The crystallization temperatures of the more highly concentrated compositions of this invention were equivalent to or, desirably, lower than that of the commercial material. Table 3 summarizes the data.

TABLE 3

|  | Stabrom 909 | Example 1 | Example 2 |
|---|---|---|---|
| Crystallization Temperature, ° C. | −4 | −3 | −11 |

The following examples show that it is possible to prepare samples with even higher initial activity. Tests indicate that these samples are less stable than those prepared above and may solidify upon storage at room temperature.

EXAMPLE 5

The procedure of Example 1 was followed. The round-bottom flask was charged with 814 g Stabrom 909 biocide. Water distilled over from 31-33° C. at a bath temperature of 42-52° C. The distillation was stopped after 3½ hours. Analysis by the KI/thiosulfate method indicated an activity at this point of 20.08% (200,800 ppm wt/wt) as active bromine. The distillation was restarted the next day and continued for an additional ½ hour. The amount of product remaining in the distillation flask was 578 g. It was dark orange with a small amount of white solid. The product was filtered through a fritted glass funnel to afford 541 g of filtrate. Analysis by the KI/thiosulfate method indicated an activity of 21.74% as Active bromine.

EXAMPLE 6

The procedure of Example 1 was followed. The round-bottom flask was charged Stabrom 909 biocide. Water distilled over from 30-37° C. at a bath temperature of 43-59° C. The distillation was stopped after 5 hours. The amount of product remaining in the distillation flask was 602 g. It consisted of a white solid and dark orange oil. The product was filtered through a fritted glass funnel to afford 438 g of filtrate and 145 g of yellow-write solid. Analysis by the KI/thiosulfate method indicated an activity of 24.10% as active bromine for the dark orange solution and 28.09% as active bromine for the solid.

EXAMPLE 7

The stabilities of the high activity BrCl samples from Examples 5 and 6 were compared to the starting sample (Control). About 100 g of the liquid products were poured into each of three 4 oz. wide-mouth polyethylene bottles. About 20 g of the solid sample from Example 6 was placed into a 4 oz. wide-mouth polyethylene bottle. The bottles were loosely capped and placed in a recirculating air oven at 47° C. The samples were periodically removed and analyzed for activity. Table 4 summarizes the data. As in Table 1, the values shown in Table 4 control (Stabrom 909 biocide) and the compositions of Examples 5 and 6 are in terms of wt % active bromine. Thus a value of 15.12 wt % is equivalent to 151,200 ppm (wt/wt). Again, the ½-life data is calculated from the slope of the least squares line obtained by plotting the data in the form of ln(activity at time=t)/(activity at time=0) vs. time. The data indicate that these even more highly concentrated samples had lower storage stability than the stating material.

TABLE 4

| Days at 47° C. | Control, wt % | Example 5, wt % | Example 6, solution, wt % | Example 6, solid, wt % |
|---|---|---|---|---|
| 0 | 15.12 | 21.70 | 24.06 | 27.84 |
| 9 | 14.76 | 19.45 | 20.28 | 24.82 |
| 21 | 14.35 | 16.99 | 16.95 | 20.46 |
| 42 | 13.73 | 14.63 | 12.63 | 13.07 |
| 56 | 13.37 | 13.67 | 10.65 | 10.64 |
| ½-Life (days) | 303 | 60 | 42 | 47 |

EXAMPLE 8

Samples of the high activity BrCl products from Examples 5 and 6 were stored at room temperature (ca. 23° C.) in the dark. The samples were periodically removed and analyzed for activity. Table 5 summarizes the data. The data indicate that the very highly concentrated samples again had lower storage stability when compared to the sample of Stabrom 909 biocide. The liquid sample from Example 6 solidified upon storage at room temperature for several weeks. That solidified sample was heated to reliquefy it prior to analysis.

TABLE 5

| Days at RT | Stabrom 909, wt % | Example 5, wt % | Example 6 solution, wt % | Example 6 solid, wt % |
|---|---|---|---|---|
| 0 | 15.12 | 21.70 | 24.06 | 27.84 |
| 35 | 15.03 | 21.52 | 23.30 | 27.89 |
| 70 | 14.93 | 21.32 | 23.36 | 27.13 |
| ½-Life (weeks) | 537 | 385 | 237 | 270 |

It will be appreciated that the highly concentrated aqueous active bromine-containing biocidal solutions of this invention can be prepared directly without a dewatering operation by suitably proportioning the amount of water in the reaction between (a) the bromine, bromine chloride or a mixture of bromine chloride and bromine and (b) an overbased aqueous solution of alkali metal salt of sulfamic acid. Thus compositions of this invention having dissolved active bromine contents in the range of above about 160,000 ppm (wt/wt) to about 215,000 ppm (wt/wt) can be prepared directly by mixing the components of (a) and (b) in the appropriate proportions. The dewatering procedure as applied to Stabrom 909 biocide in Examples 1, 2, 5, and 6 was used merely as a matter of convenience, as it avoided the need for additional synthesis reactions to prepare the samples for evaluation.

As noted above, another aspect of this invention is the discovery that it is possible to prepare new, solid state bromine-containing biocidal compositions which are suitable for storage and shipment in the solid state and which can be used either as an effective biocidal additive for direct addition in the form of solids to industrial or recreational water systems or as the raw material for the formation of highly active aqueous biocidal solutions or slurries of any desired concentration for addition to industrial or recreational water systems. Such new compositions can be formed by removal of water from an aqueous solution or slurry of a derivative product of (i.e., a product formed from) (a) bromine, bromine chloride or a mixture of bromine chloride and bromine and (b) the overbased solution of alkali metal salt of sulfamic acid. If heat is applied to the solution or slurry, the storage stability of the resultant particulate solid product tends to be lower than that of the aqueous concentrate currently available commercial as Stabrom 909, but as long as the temperature is not too high, the storage stability of the solids is adequate for short term storage. In a preferred embodiment of this invention, there is provided a spray-dried product formed from (a) bromine, bromine chloride or a mixture of bromine chloride and bromine and (b) an overbased aqueous solution of alkali metal salt of sulfamic acid (preferably a sodium salt of sulfamic acid). The evaporation of the water from the sprayed droplets provides a localized cooling effect on the particles and thus the solids can be formed at temperatures that are below the temperature of the gaseous atmosphere in which the solids are being formed. Thus spray dried products of this invention if removed from the heated environment and maintained at ambient room temperatures have better stability than if the solids are formed by evaporating the water from a non-sprayed solution or slurry at the same temperature as used in a spray drying operation. Typically the spray-dried solid state products of this invention are prepared with the temperature of the atmosphere in which the solution (or slurry) is sprayed being in the range of about 20 to about 100° C. and preferably in the range of about 20 to about 60° C. Average residence times of solids within heated spray drying zones is preferably kept short, e.g. within the range of about 1 to about 30 minutes and preferably within the range of about 1 to about 10 minutes. As a general rule, the higher the temperature, the lower should be the residence time. It is possible to spray dry within a zone maintained at reduced pressure and this enables spray drying without application of heat.

One preferred use of the new, solid state bromine-containing biocidal compositions of this invention is as a biocide for subterranean use in oil field operations. For this use this invention provides as an article of manufacture, a package comprised of (A) a water-dissolvable container (preferably a water-dissolvable bag) containing (B) a solid state bromine-containing biocidal composition formed by removal of water from an aqueous solution or slurry of a derivative product of (i.e., a product formed from) (a) bromine, bromine chloride or a mixture of bromine chloride and bromine (preferably (i) bromine chloride or (ii) a mixture of bromine chloride and bromine in which less than 50 mole percent of the mixture is bromine) and (b) an overbased aqueous solution of alkali metal salt of sulfamic acid, (preferably a sodium salt of sulfamic acid). Such solid state bromine-containing biocidal composition is preferably in the form of water-soluble particles, granules, pellets, or powder. The sizes of such particles, granules, pellets, or powder is not critical. All that is required is that the solids dissolve at a reasonably rapid rate (e.g., within about 30 minutes when in contact with water at a temperature of at least 20° C.). In a preferred embodiment the solid state bromine-containing biocidal composition of (B) in such package is a spray-dried product as described above.

Examples 9 and 10 serve to illustrate formation of solid state bromine-containing biocidal compositions of this invention.

EXAMPLE 9

This example simulates a spray drying operation that can be carried out on Stabrom 909 biocide or any other aqueous solution or slurry of a product formed from (a) bromine, bromine chloride or a mixture of bromine chloride and bromine and (b) an overbased aqueous solution of alkali metal salt of sulfamic acid. A sample of Stabrom 909 biocide (1.50 g, activity=15.10%, as Active bromine) was added in discrete drops into a crystallizing dish. The dish was placed in a recirculating oven set at 40° C. overnight. The next day, the drops were semisolid. The semisolids were manipulated with a spatula to expose the interior of the drops to air. The material was placed back into the oven for 5 additional hours. A yellow, slightly waxy solid was obtained (0.65 g). The activity of the solid was 33.24% as active bromine. After 3 days storage at room temperature in the dark, the activity of the solid was 33.38% as active bromine. After 14 days of storage at room temperature in the dark, the activity of the solid was 33.23% as Active bromine.

EXAMPLE 10

The procedure of Example 9 was repeated on a larger scale. A sample of Stabrom 909 biocide (4.00 g) was added in discrete drops into a crystallizing dish. The dish was placed in a recirculating oven set at 40° C. overnight. The next day, the drops were semisolid. The semisolids were manipulated with a spatula to expose the interior of the drops to air. The material was placed back into the oven for an additional 24 hours. A yellow, slightly waxy solid was obtained. The activity of the solid was 31.99% as active bromine. After 7 days storage at room temperature in the dark, the activity of the solid was 32.27% as active bromine. After 82 days storage at room temperature, the activity of the solid was 30.75% as active bromine.

The data in Examples 9 and 10 serve to illustrate the satisfactory stability for the solid products produced by the simulated spray drying technique. Since the solids were exposed to 40° C. for relatively long periods of time, especially in Example 10, the formation of the solids in an actual spray dryer with shorter exposures to drying temperatures should provide spray dried products of this invention having very desirable storage stability, especially if the solids are protected against exposure to excessive heat and excessive exposure to light during storage.

For convenience, the solid state bromine-containing biocidal compositions of this invention can also be referred to as sulfamate-stabilized active bromine-containing solids. In one embodiment of this invention the sulfamate-stabilized active bromine-containing solids are in the form of a powder or finely-divided particles. In another embodiment of this invention the sulfamate-stabilized active bromine-containing solids are in the form of shapes comprised of agglomerated or compressed particles. Examples of such shapes are nuggets, granules, caplets, tablets, briquettes, pucks, and the like. While there are no hard and fast rules governing differentiation with respect to size among nuggets, granules, caplets, tablets, briquettes, and pucks, typically nuggets and granules are regarded as being particles typically ranging in size from about 80 to about 3 U.S. standard mesh size. Caplets generally are in the range of about 0.5 to about 1 inch in length and with a cross-sectional width in the range of about 0.25 to about 0.5 inch. Tablets typically fall in the range of from about 0.5 to about 1.0 inch in diameter and about 0.5 to about 1.0 inch in thickness. Briquettes will normally range in size from about 0.5 to about 4.0 inches in length, from about 0.5 to about 4.0 inches in width, and from about 0.5 to about 2.5 inches in height. Pucks are normally disc-shaped objects having a diameter up to about 3.0 inches and a thickness in the range of about 0.5 to about 1.0 inch. For purposes of this invention, powders and particulate forms of the sulfamate-stabilized active bromine-containing solids of this invention are regarded as having particle sizes below about 80 U.S. standard mesh size. It will be understood and appreciated however, that the foregoing dimensions are illustrative and are not intended to unduly limit the scope of this invention.

The formation of nuggets, granules, tablets, or other compressed shapes such as briquettes and pucks from the powdery or particulate solid state sulfamate-stabilized active bromine-containing solids of this invention can utilize conventionally known processing equipment and, for the most part, known procedures. However, in conducting compaction of the blends of this invention, it is important that the compaction pressure be sufficient, whether or not a binding agent is used, to induce interparticulate binding of the particles one to another, and which may be accompanied by plastic deformation of some or most, if not all, of the particles. At the same time, the compaction pressure should not be so great as to produce a compacted product which delaminates. Typically, suitable compaction pressures fall within the range of about 1000 to about 30,000 psi, and preferably in the range of about 5000 to about 25,000 psi. Such compaction can be conducted using, for example, a rotary tableting press operated at conventional rotational speeds. Another method for accomplishing the compaction is by means of pressure extrusion through a die orifice, while concurrently shearing the extrudate to produce compacted shapes of the desired size. In such operations, the compaction pressures within the die should be sufficient to induce plastic deformation and interparticulate binding of the particles, but insufficient to produce a compacted product which, when extruded, undergoes an elastic recovery of a magnitude that causes delamination of the compacted extrudate.

Finely-divided waxes that are compatible with the sulfamate-stabilized active bromine-containing solids of this invention such as finely-divided paraffin wax and chloroparaffin wax can be used as binding agents or binders in forming the compressed shapes of this invention. Certain inorganic salts can also be used to assist in forming the compressed or compacted solids of this invention.

Also, various micronized synthetic waxes can be used as binders in forming the compacted or compressed nuggets, granules, tablets, or other compressed shapes such as briquettes and pucks from the powdery or particulate solid state sulfamate-stabilized active bromine-containing solids of this invention. Such micronized waxes are typically micronized polyolefin waxes, or micronized polyfluorocarbon waxes, or mixtures thereof. While the average particle size of the wax can vary within reasonable limits, preferred micronized waxes typically have, prior to compaction, an average particle size of no greater than about 15 microns. Similarly, preferred micronized waxes typically have, prior to compaction, a maximum particle size of no greater than about 40 microns. In most cases, the micronized wax has, prior to compaction, a bulk density in the range of about 0.9 to about 1.4 grams per cc at 25° C. Another characteristic of preferred micronized waxes is that they at least partially melt at a temperature in the range of about 100° C. to about 150° C.

Among particularly preferred micronized polyethylene waxes are those which, prior to compaction, (a) melt at a temperature in the range of about 109° C. to about 111° C., or (b) have an average particle size in the range of about 6.0 to about 8.0 microns, or (c) a maximum particle size of about 22 microns, or (d) have a combination of any two or all three of (a), (b), and (c).

Included among particularly preferred polypropylene waxes, are those materials which are characterized, prior to compaction, by having (a) a melting temperature in the range of about 140° C. to about 143° C., or (b) an average particle size in the range of about 5.0 to about 7.0 microns, or (c) a maximum particle size of about 22 microns, or a combination of any two or all three of (a), (b), and (c).

Particularly preferred micronized wax blends include micronized polyolefin and polyfluorocarbon wax blends which, prior to compaction, at least partially melt at a temperature in the range of about 104° C. to about 126° C. Among these blends are those which, prior to compaction, (a) partially melt at a temperature in the range of about 104° C. to about 110° C., or (b) have an average particle size in the range of about 5 to about 7 microns, or (c) have a maximum particle size of about 22 microns, or (d) have a combination of any two or all three of (a), (b), and (c). Also included among these blends are those which, prior to compaction, (a) partially melt at a temperature in the range of about 124° C. to about 126° C., or (b) have an average particle size in the range of about 9 to about 11 microns, or (c) have a maximum particle size of about 31 microns, or (d) have a combination of any two or all three of (a), (b), and (c).

Other particularly preferred micronized waxes are modified polyfluorocarbon waxes which, prior to compaction, (a) partially melt at a temperature in the range of about 108° C. to about 115° C., or (b) have an average particle size in the range of about 5 to about 6 microns, or (c) have a maximum particle size of about 22 microns, or (d) have a combination of any two or all three of (a), (b), and (c).

In forming the compressed or compacted shapes, a dry powder blend of the powdery or particulate solid state sulfamate-stabilized active bromine-containing solids of this invention and one or more binding agents or binders is formed and subjected to compaction or compression. Various methods can be used in forming such dry blends of this invention. Among preferred methods are use of ribbon blenders or tumble blenders for mixing the powdery or finely-divided particulate solid state sulfamate-stabilized active bromine-containing solids and the binding agent(s), such as a micronized wax. Equipment of this type is readily available in the marketplace from a number of reputable suppliers. The amount of the binding agent such as a micronized wax in the dry blends of this invention will fall within the range of about 0.5 to about 10 wt %, and preferably in the range of about 1 to about 5 wt %, based on the total weight of the solid state sulfamate-stabilized active bromine-containing solids and the binding agent. It will be understood and appreciated that departures from these ranges are permissible without departing from the scope of this invention, whenever such departures are deemed necessary or appropriate.

When carrying out compaction of powdery or particulate solid state sulfamate-stabilized active bromine-containing solids of this invention with or without one or more binding agents, it is desirable, but not essential, to apply a pressure agglomeration lubricant to the compaction surfaces of the tooling so as to reduce the coefficient of friction between the material being compacted and the tooling. When using such lubricant, it is possible to utilize any of a variety of lubricants conventionally used for this purpose, such as for example a suitable finely-divided wax or the like.

Nuggets, granules, tablets, briquettes, and pucks of this invention are of particular utility as biocidal agents used for treating swimming pools, spas, decorative fountains, toilet bowls, urinals, cooling towers, air washer systems, waste water, liquids used and formed in pulp and paper processing operations, and liquids used and formed in oil field applications such as secondary oil field recovery operations, especially operations involving seawater flooding.

In another embodiment, alkali metal dichlorohypobromite, M[BrCl$_2$] (M=alkali metal) is preformed by pre-mixing bromine chloride with aqueous sodium chloride, and the bromine chloride is used in this form to provide the active bromine content of the resultant solution. The preferred alkali metal dichlorohypobromite is sodium dichlorohypobromite.

A preferred way of forming the above aqueous biocide compositions comprising water having in solution therein an active bromine content of at least about 100,000 ppm (wt/wt), and from about 145,000 ppm to about 160,000 ppm (wt/wt) and, pursuant to this invention in the range of above about 160,000 ppm (wt/wt) to about 215,000 ppm (wt/wt) of active bromine, is to mix together (i) bromine chloride or a combination of bromine chloride and bromine, and (ii) an overbased aqueous solution of alkali metal salt of sulfamic acid, or (iii) water, alkali metal base, and an alkali metal salt of sulfamic acid, or (iv) water, an alkali metal base, and sulfamic acid, or (v) any combination of (ii), (iii), and (iv), and in relative proportions of such that the atom ratio of nitrogen to active bromine in said biocide composition is greater than 0.93, preferably greater than 1, and the pH of the biocide composition is at least 7 (e.g., in the range of about 10 to about 13.5), and preferably in the range of about 12 or 12.5 to about 13.5 or 14.

In each of the embodiments of this invention, the atom ratio of nitrogen to active bromine is preferably in the range of about 1.1 to about 1.5, and more preferably in the range of from about 1.35 to about 1.5. Still higher ratios can be employed, if desired.

As noted above, amounts of active bromine above 160,000 ppm (wt/wt) are within the scope of this invention. In other words, any concentration of the stabilized active bromine component(s) above about 160,000 ppm (wt/wt) that does not result in precipitate formation during storage or transportation of the concentrated solution under normal ambient temperature conditions (e.g., 23° C.) constitute compositions of this invention. When used for microbiological control, the concentrated solutions of this invention are mixed or diluted with, or introduced into, additional water, which typically is the water being treated for such microbiological control, so that the amount of active bromine in the water being treated for microbiological control is a microbiologically effective amount. The various compositions of the embodiments referred to in this paragraph preferably additionally contain dissolved chloride ion, most preferably in the presence of a stoichiometric excess of alkali metal cation, such as sodium or potassium cations. In contrast to certain other alkali metal salts, the alkali metal chloride salts have high solubilities in the aqueous medium of the concentrates of this invention, and thus pose no problem with respect to precipitate formation during storage, transportation, or use. In addition, the dissolved alkali metal chloride in the solutions of this invention minimize the extent to which oxygen or air becomes dissolved in the concentrated solutions.

Although not mandatory, it is preferred that from the inception of their production the compositions of this invention are and remain at all times free of peroxides.

Still other embodiments of this invention include the following:

1) A concentrated aqueous biocidal composition containing sulfamate-stabilized bromonium ion, such composition (i) from its inception, having a pH in excess of 8 and (ii) having greater than about 16 wt % bromonium ion present in solution, measured as $Br_2$, such wt % being based on the total weight of the composition.
2) A concentrated biocidal composition as in 1) where from its inception, the composition has a pH greater than 10.
3) A concentrated aqueous biocidal composition containing stabilized oxidizing halogen obtained by the reaction of $BrCl$ and $^{\ominus}SO_3NH_2$, such composition (i) having in solution greater than 16 wt % bromonium ion, measured as $Br_2$, such wt % being based upon the total weight of the composition, and (ii) having a pH greater than 10.
4) A concentrated aqueous biocidal composition containing stabilized oxidizing halogen obtained by the reaction of $BrCl$ and $^{\ominus}SO_3NH_2$, such composition containing at least about 16 wt % bromonium ion in solution, measured as $Br_2$, such wt % being based upon the total weight of the composition.

Preferably, but not necessarily, the composition of 1), 2), 3), and 4) immediately above are further characterized by comprising chloride ion in solution therein.

A preferred alkali metal salt of sulfamic acid, and a preferred alkali metal base used in forming such salt are, respectively, potassium sulfamate and a potassium base such as KOH. Most preferred are, respectively, sodium sulfamate, and a sodium base such as NaOH.

One desirable way of accomplishing the mixing of the reactants when producing the concentrated liquid biocide formulations of this invention comprises concurrently introducing (a) bromine chloride and (b) an aqueous solution of alkali metal salt of sulfamic acid into a reaction zone, such as a reactor or other reaction vessel, and having the pH of the resulting solution at least at 7 (e.g., in the range of about 10 to about 13.5), and preferably in the range of about 12 or 12.5 to about 13.5 or 14. As noted above, the proportions of (a) and (b) used are such that (i) the active bromine content of the solution is at least about 100,000 ppm (wt/wt), e.g., from about 145,000 to about 160,000 ppm (wt/wt) and pursuant to this invention, is in the range of greater than about 160,000 ppm (wt/wt) to about 215,000 ppm (wt/wt) and (ii) the atom ratio of nitrogen to active bromine from (a) and (b) is greater than 0.93, preferably greater than 1.

Water treated pursuant to this invention by addition thereto of an effective biocidal amount of active bromine as a composition of this invention results in a substantial dilution since, in general, on a wt/wt basis dosages in the treated water in the range of about 0.5 to about 20 parts per million of bromine (expressed as $Br_2$) and preferably in the range of about 4 to about 10 parts per million of bromine (expressed as $Br_2$) in the aqueous medium being treated for biocidal and/or biofilm control will usually suffice. This results in highly effective microbiological control in the water being treated.

A further advantage of this invention is that it is unnecessary to produce the concentrated aqueous biocide compositions of this invention by use of powerful oxidants such as ozone or peroxides, which are known to possess undesirable, and indeed, hazardous characteristics.

The following additional Examples are presented for purposes of illustration and not limitation.

EXAMPLES 11-17

Various compositions were prepared using the above general procedure and the active bromine content of the resultant compositions was determined analytically. The conditions used and results obtained (observations on odor and vapor, and initial contents of active bromine in the solutions) are summarized in Table 6 in which $SA_{eq}$ stands for mole ratio of sulfamic acid to halogen.

TABLE 6

Data on Prepared Sulfamic Acid Stabilized Bromine Solutions

| Ex. No. | Halogen | pH | $SA_{eq}$ | Odor and Vapor Comments | Active Bromine, wt % |
|---|---|---|---|---|---|
| 11 | $Br_2$ | 13.0 | 1.42 | Slight sweet smell, no observed vapor | 12.4%* |
| 12 | $Br_2$ | 7.0 | 1.48 | Slight Br odor, no fuming | 13.4%* |

TABLE 6-continued

Data on Prepared Sulfamic Acid Stabilized Bromine Solutions

| Ex. No. | Halogen | pH | $SA_{eq}$ | Odor and Vapor Comments | Active Bromine, wt % |
|---|---|---|---|---|---|
| 13** | BrCl | 7 | 0.92 | Strong Br odor, slight fuming | 11.2% |
| 14 | Br$_2$ | 13.0 | 1.15 | Slight sweet smell, no observed vapor | 19.6% |
| 15 | Br$_2$ | 7.0 | 1.13 | Moderate Br odor, no fuming | 26.7% |
| 16 | BrCl | 12.5 | 0.94 | Slight sweet smell, no observed vapor | 18.0% |
| 17 | BrCl | 12.8 | 1.41 | Slight sweet smell, no observed vapor | 17.6% |

*Measured with Hach spectrometer; all others titrated using starch-iodine-sodium arsenite method.
**Comparative example.

The specific details for Examples 13-17 of Table 6 are given below. Example 19 illustrates a process wherein an alkali metal dichlorohypobromite is utilized as the source of active bromine.

EXAMPLE 13

Bromine Chloride, Caustic and Sodium Sulfamate at Neutral pH

A 1 liter flask was charged with 52.0 g of sulfamic acid and 250 g of water. Sodium sulfamate was prepared by adding 60.0 g of 50% sodium hydroxide to the stirred slurry. Bromine chloride was prepared by adding 20 g of chlorine to 47.0 g of bromine. This bromine chloride was then co-fed with 210 g of 25% sodium hydroxide to maintain the pH between 6 and 8. 5 mL of 1 M Hydrochloric Acid were added to bring the final pH to approximately 7±0.5. The solution, which contained some solids, was transferred to an amber bottle for storage. Starch-iodine titration of a sample of the solution indicated that it had an active bromine concentration of 11.2%.

EXAMPLE 14

Bromine, Caustic (50% Sodium Hydroxide) and Sodium Sulfamate

A 500 mL flask was charged with 26.0 g of sulfamic acid and 50 g water. To this slurry was added 35.0 g of 50% sodium hydroxide. As the acid was converted to the sodium salt, it dissolved into the aqueous solution more readily. Bromine (37.0 g) and 50% sodium hydroxide (30.0 g) were co-fed into the solution at a rate which maintained the pH between 11 and 13. After all of the bromine and caustic had been added, the contents were transferred to an amber bottle for storage. Starch-iodine titration of a sample of the solution indicated that it had an active bromine concentration of 19.6%. Analysis of the bromine solution still contained more than 95% of its active bromine content.

EXAMPLE 15

Bromine, Caustic and Sodium Sulfamate at Neutral pH

A 500 mL flask was charged with 26.0 g of sulfamic acid and 50 g of water. To this stirred slurry was added 30.9 g of 50% sodium hydroxide, which raised the initial pH to approximately 12. The sulfamic acid then dissolved into solution. Bromine (37.7 g) was fed into the solution until the pH dropped to approximately 7, when 50% sodium hydroxide (10.9 g) was co-fed to maintain the pH between 6 and 9. 5 mL of 0.01 N sodium hydroxide was used to bring the final pH to approximately 7±0.5. The contents were then transferred to an amber bottle for storage. Starch-iodine titration of a sample of this solution indicated that it had an active bromine content of 26.7%. Analysis of the solution after six weeks of storage at ambient temperature indicated that the stabilized bromine solution still contained more than 95% of its active bromine content.

EXAMPLE 16

Bromine Chloride, Caustic and Sodium Sulfamate

A 1 liter flask was charged with 107 g of sulfamic acid and 200 g of water. Sodium sulfamate was prepared by adding 93.9 g of 50% sodium hydroxide to the stirred slurry. Bromine chloride was prepared by adding 39 g of chlorine to 96.0 g of bromine. This bromine chloride was the co-fed with 319 g of 50% sodium hydroxide to maintain the pH between 11 and 13. After stirring for an additional 30 minutes, the solution, which contained some solids, was transferred to an amber bottle for storage. Starch-iodine titration of a sample of the solution indicated that it had an active bromine concentration of 18.0%. Analysis of the solution after three weeks at ambient temperature indicated that the stabilized bromine solution still contained more than 90% of its active bromine content.

EXAMPLE 17

Bromine Chloride, Caustic and Sodium Sulfamate; Larger Scale

A 5 liter flask was charged with 470 g of sulfamic acid and 900 g of water. Sodium sulfamate was prepared by adding 436 g of 50% sodium hydroxide to the stirred slurry. Bromine chloride was prepared by adding 120 g of chlorine to 276 g of bromine. This bromine chloride was the co-fed with 1723 g of 50% sodium hydroxide to maintain the pH between 12 and 13. After stirring for an additional 60 minutes, the orange, clear solution was transferred to an polyethylene bottle for storage. Starch-iodine titration of a sample of the solution indicated that it had an active bromine concentration of 17.6%.

EXAMPLE 18

Bromine Chloride, Caustic and Sodium Sulfamate; Larger Scale

A 5 liter flask was charged with 390 g of sulfamic acid and 400 g of water. Sodium sulfamate was prepared by adding 1820 g of 25% sodium hydroxide to the stirred slurry while cooling to keep the temperature below 30° C. 344 g of bromine chloride was then added. The orange, clear solution had a pH of 13.5, and was filtered and transferred to a polyethylene bottle for storage. Starch-iodine titration of a sample of the solution indicated that it had an active bromine concentration of 16.2%.

EXAMPLE 19

Reducing Vapor Pressure of Sodium Dichlorohypobromite with Sodium Sulfamate

Sodium sulfamate was prepared by slurrying 24.3 g of sulfamic acid in 9 g of water. 24.0 g of 50% sodium hydroxide was added dropwise. The flask heated noticeably and the solid dissolved. This solution was dropped into 184.6 g of sodium dichlorohypobromite. Sodium dichlorohypobromite, Na[BrCl$_2$] is prepared by adding 30.6 g of bromine chloride to 154 g of 3M aqueous sodium chloride. An additional 24 g of 50% sodium hydroxide was added to raise the pH to 7. Analysis of this solution indicated that it had an active bromine concentration of 12.0%.

At present, a preferred way of conducting the process of this invention on a larger scale involves charging to a reactor water, aqueous alkali metal hydroxide solution (preferably aqueous sodium hydroxide solution), sulfamic acid, and then bromine chloride or a mixture of bromine chloride and bromine. Preferred proportions of the components are 17 parts by weight of water, 59 parts by weight of a 25 wt % aqueous sodium hydroxide solution, 13 parts by weight of sulfamic acid, and 11 parts by weight of bromine chloride, for a total of 100 parts by weight. Preferably these components are charged in the order named. However, as long as the bromine chloride is charged last, the order of addition of the other three components can be varied. The bromine chloride used preferably contains in the range of 68.9 to 73.1 wt % bromine. However, pure bromine chloride or other combinations of bromine chloride and bromine can be used to make effective product, if desired. The temperature of the mixture during the addition of the bromine chloride is preferably not allowed to exceed 50° C., although the temperature can be allowed to go above 50° C. for short periods of time without detrimental effects. Prolonged exposure to elevated temperatures tends to cause degradation of the product, and thus should be avoided. The bromine chloride concentration in the resultant product solution as formed in this manner (and in whatever chemical form or forms the active bromine chloride exists in such solution), is in the range of greater than 16.0 wt % to about 21.5 wt % (e.g, between 165,000 and 215,000 ppm (wt/wt)), and preferably is targeted at an active bromine content in the range of about 17.6 wt % to about 19.0 wt % (i.e., in the range of about 176,000 ppm wt/wt to about 190,000 ppm wt/wt) or at an active bromine content in the range of about 20.1 wt % to about 21.5 wt % (i.e., in the range of about 201,000 ppm wt/wt to about 215,000 ppm wt/wt). Determination of such concentration can, of course, be readily accomplished by starch-iodine titration. When operating as described in this paragraph, the final pH of the product solution is in the range of about 12.4 to about 13.7. It will be understood and appreciation that pursuant to this invention an equivalent amount of bromine or bromine and chlorine can be used in this processing in lieu of bromine chloride or mixtures of bromine chloride and bromine.

Another preferred way of operating on a larger scale the process described in the immediately preceding paragraph is in a semi-continuous or semi-batch mode. This involves forming the alkali metal sulfamate solution, preferably a sodium sulfamate solution (using caustic, water, sulfamic acid), and feeding in the bromine chloride or bromine chloride and bromine (BrCl) to a suitable vessel (reactor, tank, etc.) containing the sulfamate solution. The BrCl may go straight into the vessel of the aqueous sodium sulfamate or into a pumparound loop on the vessel. The BrCl may be made up ahead of time, or can be made by continuously mixing the bromine and chlorine together in a pipe, with or without a mixing element, and then injecting it straight into the aqueous sodium sulfamate without isolating the BrCl. The advantage of continuously making the BrCl is that this avoids having a separate BrCl reactor or storage tank and the need for keeping a large quantity of this material in storage on plant facilities.

Besides being useful in the microbiocidal treatment of aqueous media such as recreational water, industrial cooling water, process water, and wastewater, the concentrated solutions of this invention can be used for eradicating, or at least reducing, biofilm on surfaces contacted by aqueous media such as cooling tower surfaces, filter surfaces, surfaces in pools and spas, interior surfaces of pipes and conduits, and similar surfaces on which biofilm can develop. Besides causing damage and/or unsightliness to the surfaces to which the bacterial films become tenaciously attached, biofilms can harbor dangerous pathogens. And because they can form slime layers, biofilms can interfere with normal water flow. Despite the fact that the slimy films themselves constitute protective barriers against penetration of biocidal agents, the biocidal solutions of this invention enable effective biocidal control of biofilms. Thus pursuant to this invention the concentrated aqueous solutions of this invention can be used for introducing biocidally effective amounts of active bromine into aqueous systems that come into contact with surfaces infested with biofilm and thereby at least reduce the biofilm, if not eradicate the biofilm in its entirety. This is of course accomplished by adding an amount of a concentrated aqueous solution of this invention to the water to be treated for biofilm reduction or eradication, the amount of such addition being an amount (dosage) that will at least reduce the biofilm, if not eradicate the biofilm in its entirety. Generally speaking, dosages in the range of about 0.5 to about 20 parts per million of active bromine (expressed as $Br_2$) and preferably in the range of about 4 to about 10 parts per million of active bromine (expressed as $Br_2$) in the aqueous medium being treated for biofilm control will usually suffice, but lesser or greater amounts of active bromine can be used whenever deemed necessary, appropriate, or desirable. Naturally there may be some period of time that will pass between the time that the concentrated aqueous solution of this invention is brought into contact with, and thus diluted in, the water being treated, and the time that the biofilm is reduced or eradicated. If desired, such reduction or eradication can be observed by periodically visually inspecting the water-contacted surfaces that are infested with the biofilm, assuming such surfaces are in a location that one can observe. In the case of filters, conduits, or pipes infested with biofilm and carrying water treated pursuant to this invention with a biocidal amount (dosage) of a concentrated aqueous solution of this invention to reduce or eradicate such biofilm, the reduction or eradication of biofilm may be evidenced and thus observed by improved performance of the apparatus (e.g., increased water flow). But whether or not such observations are made, when a biocidally effective amount of active bromine is included in the water that comes in contact with the biofilm after addition to such water of a suitable dosage of a concentrated solution of this invention, reduction or eradication of the biofilm will occur.

Amounts of the solid state biocidal compositions of this invention that are used are also amounts sufficient to effectively control the microorganisms, biofilm and/or other pathogens to be controlled. Thus amounts of such solid state products yielding aqueous solutions containing, e.g., in the range of about 0.5 to about 20 parts per million of active bromine (expressed as $Br_2$) and preferably in the range of about 4 to about 10 parts per million of active bromine (expressed as $Br_2$) in the aqueous medium being treated for biofilm control will usually suffice, but once again lesser or greater amounts of active bromine can be used whenever deemed necessary, appropriate, or desirable. One preferred use of the solid state products of this invention is in control of bacteria and other microorganisms present in subterranean locations such as in holes being drilled or serviced in oil and/or gas fields. For this purpose, this invention provides a water-dissolvable or water-disintegratable container or bag containing a suitable microbiocidal dosage of a solid state biocidal agent or composition of this invention. Such packages comprised of containers or bags of the solid state biocidal agent of this invention can simply be dropped into the hole. Upon reaching the water level in the hole, the biocidal agent of this invention rapidly dissolves in the water and thereby provides powerful microbiocidal against microorganisms present in well being drilled or serviced, including various anaerobic species and sessile bacteria. The amount of the solid state biocidal agent contained in the package will depend upon the such factors as the size of the hole and extent of microbial activity to be controlled. Thus the amount of the biocidal agent for use in the package can readily be determined in any given case by conducting a few test test runs. An advantage of the solid state biocidal agents of this invention is that they can be effectively used in amounts well in excess of the quantity actually needed to effect the biocidal activity without encountering significant adverse consequences. Thus precise control of amounts used in a given downhole treatment is ordinarily not required.

Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients, or if formed in solution, as it would exist if not formed in solution, all in accordance with the present disclosure. It matters not that a substance, component or ingredient may have lost its original identity through a chemical reaction or transformation during the course of such contacting, blending, mixing, or in situ formation, if conducted in accordance with this disclosure.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A solid state bromine-containing biocidal composition formed by removal of the water from an aqueous solution or slurry of a product formed in water from (A) (i) bromine chloride, (ii) a mixture of bromine chloride and bromine, (iii) bromine and chlorine in a $Br_2$ to $Cl_2$ molar ratio of at least 1 or about 1, or (iv) bromine chloride, bromine, and chlorine in proportions such that the total $Br_2$ to $Cl_2$ molar ratio is at least 1 or about 1; and (B) (i) alkali metal salt of sulfamic acid and/or sulfamic acid, and (ii) alkali metal base, wherein said aqueous solution or slurry has a pH of at least 7 and an atom ratio of nitrogen to active bromine from (A) and (B) of greater than 0.93, wherein said composition is a spray-dried composition.

2. A composition of claim 1 wherein said pH is in the range of about 10 to about 13.5, and wherein said atom ratio is greater than 1.

3. A composition of claim 1 wherein said pH is in the range of about 12.5 to about 13.5.

4. A composition of claim 1 wherein said pH is in the range of about 12 to about 14.

5. A composition of any of claims 1-4 wherein the alkali metal of the alkali metal salt of sulfamic acid and of the alkali metal base is sodium or potassium.

6. A composition of any of claims 1-4 wherein the alkali metal of the alkali metal salt of sulfamic acid and of the alkali metal base is sodium.

7. An article of manufacture in the form of a package for use in oilfield or gasfield operations, said package comprising a container that dissolves or disintegrates in water and that contains a dissolved solid state bromine-containing biocidal composition of claim 1 whereby on coming into contact with downhole water in a well being serviced and/or (ii) a subterranean hole being drilled, the dissolving or disintegration of the container enables the downhole water and the biocidal composition to come in contact with each other and thereby provide biocidal activity to the downhole water.

8. An article of manufacture as in claim 7 wherein said solid state bromine-containing biocidal composition is (i) in the form of a powder or finely divided particles, or (ii) in the form of shapes comprised of agglomerated or compressed particles.

9. A process of forming a solid state bromine-containing biocidal composition, which process comprises removing the water from an aqueous solution or slurry of a product formed in water from (A) (i) bromine chloride, (ii) a mixture of bromine chloride and bromine, (iii) bromine and chlorine in a $Br_2$ to $Cl_2$ molar ratio of at least 1 or about 1, or (iv) bromine chloride, bromine, and chlorine in proportions such that the total $Br_2$ to $Cl_2$ molar ratio is at least 1 or about 1; and (B) (i) alkali metal salt of sulfamic acid and/or sulfamic acid, and (ii) alkali metal base, wherein said aqueous solution or slurry has a pH of at least 7 and an atom ratio of nitrogen to active bromine from (A) and (B) of greater than 0.93, wherein the water is removed from said aqueous solution or slurry by spray drying said aqueous solution or slurry.

10. A process of claim 9 wherein the water is removed from an aqueous slurry of a product formed in water from (A) and (B).

11. A process of claim 9 wherein the water is removed from an aqueous solution of a product formed in water from (A) and (B).

12. A process of claim 9 wherein said pH is in the range of about 12.5 to about 13.5.

13. A process of claim 9 wherein said pH is in the range of about 12 to about 13.5.

14. A process of forming a solid state bromine-containing biocidal composition, which process comprises removing the water from an aqueous solution or slurry of a product formed in water from (A) (i) bromine chloride, (ii) a mixture of bromine chloride and bromine, (iii) bromine and chlorine in a $Br_2$ to $Cl_2$ molar ratio of at least 1 or about 1, or (iv) bromine chloride, bromine, and chlorine in proportions such that the total $Br_2$ to $Cl_2$ molar ratio is at least 1 or about 1; and (B) (i) alkali metal salt of sulfamic acid and/or sulfamic acid, and (ii) alkali metal base, wherein said aqueous solution or slurry has a pH of at least 7 and an atom ratio of nitrogen to active bromine from (A) and (B) of greater than 0.93, and wherein the resultant product is dried by spray drying.

15. A process of any of claim 9, 10, 11, or 14 wherein the spray drying takes place
   (A) in the atmosphere of a spray drying zone, the temperature(s) of said atmosphere being in the range of about 20 to about 60° C. and wherein the average residence time of solids within a heated spray drying zone is kept within the range of about 1 to about 10 minutes; or
   (B) within a zone maintained at reduced pressure without application of heat.

16. A process as in claim 15 wherein said aqueous solution or slurry is sprayed in accordance with (A).

17. A process of claim 15 wherein said spray drying is conducted in accordance with (B).

* * * * *

UNITED STATES PATENT AND TRADEMARK OFFICE
CERTIFICATE OF CORRECTION

PATENT NO. : 8,414,932 B2
APPLICATION NO. : 10/282290
DATED : April 9, 2013
INVENTOR(S) : Christopher J. Nalepa et al.

Page 1 of 1

It is certified that error appears in the above-identified patent and that said Letters Patent is hereby corrected as shown below:

Title page, (73) Assignee: reads Albemarie Corporation and should read -- Albemarle Corporation --.

In the Claims

Claim 13, Column 26, on line 45, reads "about 12 to 13.5." and should read -- about 12 to about 14. --.

Signed and Sealed this
Thirtieth Day of September, 2014

Michelle K. Lee
*Deputy Director of the United States Patent and Trademark Office*